United States Patent
Zhou et al.

(10) Patent No.: US 9,951,095 B2
(45) Date of Patent: Apr. 24, 2018

(54) CHROMIUM METAL ORGANIC FRAMEWORKS AND SYNTHESIS OF METAL ORGANIC FRAMEWORKS

(71) Applicant: The Texas A&M University System, College Station, TX (US)

(72) Inventors: Hong-Cai Zhou, College Station, TX (US); Tian-Fu Liu, College Station, TX (US); Xizhen Lian, College Station, TX (US); Lanfang Zou, College Station, TX (US); Dawei Feng, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/307,267

(22) PCT Filed: May 11, 2015

(86) PCT No.: PCT/GB2015/051382
§ 371 (c)(1),
(2) Date: Oct. 27, 2016

(87) PCT Pub. No.: WO2015/173553
PCT Pub. Date: Nov. 19, 2015

(65) Prior Publication Data
US 2017/0050995 A1    Feb. 23, 2017

Related U.S. Application Data

(60) Provisional application No. 61/994,713, filed on May 16, 2014.

(51) Int. Cl.
C08F 4/69       (2006.01)
C07F 11/00      (2006.01)
C07F 15/02      (2006.01)
C07F 7/28       (2006.01)

(52) U.S. Cl.
CPC ............. *C07F 11/005* (2013.01); *C07F 7/28* (2013.01); *C07F 15/025* (2013.01)

(58) Field of Classification Search
USPC ...................................... 556/57, 62
See application file for complete search history.

(56) References Cited

PUBLICATIONS

Bromberg; Chemistry of Materials; 2012, 24, 1664-675.*
Chowdhury; The Journal of Physical Chemistry C; 2009, 113, 6616-6621.*
Ferey; Angewandte Chemie International Edition; 2004, 43, 6296-6301.*
247th ACS National Meeting and Exposition (Johnson Matthey Technol. Rev., 2014, 58, (4), 205-211; Mar. 16-20, 2014).*
Alexander Schoedel et al., "The asc Trinodal Platform: Two-Step Assembly of Triangular, Tetrahedral, and Trigonal-Prismatic Molecular Building Blocks," Angew. Chem. Int. Ed. 2013, vol. 52, 2902-2905.
Alexander Schoedel et al., "Network Diversity through Decoration of Trigonal-Prismatic Nodes: Two-Step Crystal Engineering of Cationic Metal-Organic Materials," Angew. Chem. Int. Ed. 2011, vol. 50, 11421-11424.
Enrique Gonzalez-Vergara et al., "Synthesis and Structure of a Trinuclear Chromium(III)—Nicotinic Acid complex," Inorganica Chimica Acta 1982, vol. 66, 115-118.
Antonis Vlachos et al., "A nearly symmetric trinuclear chromium(III) oxo carboxylate assembly: preparation, molecular and crystal structure, and magnetic properties of [Cr3O(O2CPh)6(MeOH)3](NO3)2MeOH," Inorganica Chimica Acta 2004, vol. 357, 3162-3172.
International Search Report and Written Opinion of the International Searching Authority (EPO) for PCT/GB2015/051382 dated Sep. 21, 2015 (14 pages).

* cited by examiner

*Primary Examiner* — Pancham Bakshi
(74) *Attorney, Agent, or Firm* — Reising Ethington P.C.

(57) ABSTRACT

The present invention relates to monocrystalline metal organic frameworks comprising chromium ions and carboxylate ligands and the use of the same, for example their use for storing a gas. The invention also relates to methods for preparing metal organic frameworks comprising chromium, titanium or iron ions and carboxylate ligands. The methods of the invention allow such metal organic frameworks to be prepared in monocrystalline or polycrystalline forms.

10 Claims, 21 Drawing Sheets

CHROMIUM METAL ORGANIC FRAMEWORKS AND SYNTHESIS OF METAL ORGANIC FRAMEWORKS

This application claims the benefit of U.S. provisional application No. 61/994,713, filed on 16 May 2014, the entire contents of which are incorporated by reference.

This invention was made with government support under DE-AR0000073 awarded by U.S. Dept of Energy. The government has certain rights in the invention The present invention relates to new monocrystalline metal organic frameworks, methods for preparing the same, and the use of the same as well as new metal organic frameworks useful as intermediates in preparing the same, methods for preparing such intermediates, and the use of such intermediates in the preparation of monocrystalline metal organic frameworks. In particular, the invention relates to large single crystals of metal organic frameworks comprising chromium (Cr) ions, and to methods for preparing metal organic frameworks that comprise chromium, iron or titanium ions.

Metal-Organic Frameworks (MOFs) have garnered significant interests in the last two decades due to their promising potential in many applications such as gas adsorption, separation, catalysis and sensing. For example, see Yaghi, O. M.; O'Keeffe, M.; Ockwig, N. W.; Chae, H. K.; Eddaoudi, M.; Kim, J. Nature 2003, 423, 705. (b) Ferey, G.; Mellot-Draznieks, C.; Serre, C.; Millange, F. Acc. Chem. Res. 2005, 38, 217. (c) Horike, S.; Shimomura, S.; Kitagawa, S. Nat. Chem. 2009, 1, 695. (d) Seo, J. S.; Whang, D.; Lee, H.; Jun, S. I.; Oh, J.; Jeon, Y. J.; Kim, K. Nature 2000, 404, 982. (e) Jiang, H.-L.; Liu, B.; Akita, T.; Haruta, M; Sakurai, H.; Xu, Q. J. Am. Chem. Soc. 2009, 131, 11302. (f) Kreno, L. E.; Leong, K.; Farha, O. K.; Allendorf, M.; Van Duyne, R. P.; Hupp, J. T. Chem. Rev. 2012, 112, 1105. (g) Yang, S.; Liu, L.; Sun, J.; Thomas, K. M.; Davies, A. J.; George, M. W.; Blake, A. J.; Hill, A. H.; Fitch, A. N.; Tang, C. C.; Schröder, M. J. Am. Chem. Soc. 2013, 135, 4954. (h) Bloch, E. D.; Queen, W. L.; Krishna, R.; Zadrozny, J. M.; Brown, C. M.; Long, J. R. Science 2012, 335, 1606. (i) Wang, Z.; Cohen, S. M. Chem. Soc. Rev. 2009, 38, 1315.

Compared with other porous materials such as zeolite and mesoporous silica, MOFs are based on crystalline porous structures tunable on the atomic scale, which can be designed and functionalized by judicious choice of metal nodes and modification of the organic linkers. However, one of the limitations of most MOFs is their low chemical stability, which undoubtedly hampers their application in industry. A rule of thumb for the construction of stable MOFs comes from the simple Hard and Soft Acid and Base Theory, which guides the selection of the metal-ligand combination for a MOF. For example, see Pearson, R. G. J. Am. Chem. Soc. 1963, 85, 3533. Because the carboxylate group is a hard Lewis base, hard Lewis acids such as $Fe^{3+}$, $Cr^{3+}$, $Zr^{4+}$ and $Ti^{4+}$ are usually considered good candidates for the construction of robust MOFs. This method has become the focus of some recent research efforts but very few stable MOFs have been obtained, especially in single crystal form. For example, see (a) Cavka, J. H.; Jakobsen, S.; Olsbye, U.; Guillou, N.; Lamberti, C.; Bordiga, S.; Lillerud, K. P. J. Am. Chem. Soc. 2008, 130, 13850. (b) Ferey, G.; Serre, C. Chem. Soc. Rev. 2009, 38, 1380. (c) Phan, A.; Doonan, C. J.; Uribe-Romo, F. J.; Knobler, C. B.; O'Keeffe, M.; Yaghi, O. M. Acc. Chem. Res. 2010, 43, 58. (d). Murray, L. J.; Dincă, M.; Yano, J.; Chavan, S.; Bordiga, S.; Brown, C. M.; Long. J. R. J. Am. Chem. Soc. 2010, 132, 7856. (e) Feng, D.; Gu, Z.-Y.; Li, J.-R.; Jiang, H.-L.; Wei, Z.; Zhou, H.-C. Angew. Chem. Int. Ed. 2012, 51, 10307. (f) Jiang, H.-L.; Feng, D.; Liu, T.-F.; Li, J.-R.; Zhou, H.-C. J. Am. Chem. Soc. 2012, 134, 14690. The main reason is that MOFs based on these metal ions of high valence are difficult to crystallize. Occasionally, MOFs in the form of crystalline powder were obtained, but structure solution and refinement based on Powder X-Ray Diffraction (PXRD) data is not straightforward. Furthermore, the incorporation of rarely reported metal nodes into MOFs is less predictable and controllable.

There is also a need to provide MOFs in monocrystalline form. A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. They are different from monocrystalline materials. Large single crystals are very rare in nature and can be difficult to produce in the laboratory.

The present invention relates in particular to new monocrystalline high valance metal organic frameworks, and methods for preparing the same. Metal organic framework powder material has been prepared by various methods but prior to this invention large single crystals of chromium metal organic frameworks have not been prepared. An object of this invention, therefore, is to provide monocrystalline chromium metal organic frameworks for the first time. Another object is to provide methods for producing monocrystalline chromium, iron, and titanium metal organic frameworks.

There is therefore a need for improved methods of synthesis of metal organic frameworks. The present invention addresses this need and provides for the first time a means for preparing monocrystalline metal organic frameworks comprising Cr(III) metal ions. The invention also provides a method that provides monocrystalline chromium, iron and titanium metal organic frameworks.

In one aspect, the invention provides a monocrystalline metal organic framework comprising chromium ions, such as $Cr^{3+}$ ions, and carboxylate ligands.

In one embodiment, the metal organic framework comprises one or more metal-ligand clusters, each metal-ligand cluster comprising (i) a metals cluster having two or more metal ions, wherein at least one metal ion is chromium, and (ii) one or more ligands having two or more carboxylate groups.

In one embodiment, the metal organic framework is a single crystal. For example, the crystal may have a size greater than or equal to about 0.05 mm, 0.1 mm, 0.2 mm, 0.3 mm, 0.4 mm, 0.5 mm, 0.6 mm, 0.7 mm, 0.8 mm, or 0.9 mm. For example, the crystal size may range from About 0.1 mm to about 5 mm, preferably from about 0.3 mm to about 4 mm, more preferably from about 0.5 mm to about 3 mm, more preferably from about 1 mm to about 2 mm.

The crystal may have a size ranging from About 0.1 mm to about 2.0 mm.

In one embodiment, the metal organic framework comprises at least one metal-ligand cluster, each metal ligand cluster comprising at least one chromium metal ion. For example, the at least one metal-ligand cluster comprises at least two chromium metal ions, or the at least one metal-ligand cluster comprises three chromium metal ions.

In one embodiment, the metal cluster may have a formula of $Cr_3O$.

In one embodiment, the metal organic framework may have a $Cr_3O$ cornerstone.

In one embodiment, the chromium metal organic framework comprises metal clusters coordinated with 4, 5, or 6 ligands.

In one embodiment, the chromium metal organic framework comprises inorganic cornerstones having at least 8 coordination sites, at least 10 coordination sites, or having 12 coordination sites.

In one embodiment, the chromium metal organic framework has a molar ratio of metal ions to organic linker of from about 1:0.30 to about 1:0.55, or from about 1:0.33 to about 1:0.5.

In one embodiment, the chromium metal organic framework has a surface area of at least 1000 m$^2$/g, at least 1100 m$^2$/g, or greater than or equal to 1200 m$^2$/g. Likewise, the metal-organic framework may have a surface area of less than or equal to 6000 m$^2$/g, less than or equal to 4000 m$^2$/g, less than or equal to 3500 m$^2$/g less than or equal to 3000 m$^2$/g. For example, the chromium metal organic framework may have a surface area of from about moo to about 4000 m$^2$/g.

In one embodiment, the chromium metal organic framework comprises cavities having a free diameter of about 4 Å to about 60 Å, about 5 Å to about 50 Å, about 5 Å to about 25 Å, about 40 Å to about 60 Å, about 45 Å, or about 55 Å.

In one embodiment, the chromium metal organic framework comprises pores having a pore volume from about 0.1 cm$^3$/g to about 4 cm$^3$/g, or from about 0.2 cm$^3$/g to about 2 cm$^3$/g, or from about 1 cm$^3$/g to about 4 cm$^3$/g.

The carboxylate ligands may be selected from any suitable carboxylate ligands. A range of suitable carboxylate ligands are provided below.

In particular, the carboxylate ligands may be selected from but not limited to di-, tri-, and tetra-carboxylate ligands. For example, the carboxylate ligands may be 2',3'',5'',6'-tetramethyl-[1,1':4',1'':4'',1'''-quaterphenyl]3,3''',5,5'''-tetracarboxylate, 1,3,5-benzenetribenzoate, and 4,4',4''-s-triazine-2,4,6-triyltribenzoate.

The monocrystalline metal organic frameworks of the invention comprise $Cr^{3+}$ ions metal ions which may be octahedrally coordinated, wherein three $Cr^{3+}$ ions share a common oxygen to form a [$Cr_3(\mu$-O)] cluster. For example, each [$Cr_3(\mu$-O)] cluster may be connected with four carboxylate ligands and four aqua ligands.

The carboxylate ligands may be selected from any suitable carboxylate ligands. A range of suitable carboxylate ligands are provided below.

In particular, the carboxylate ligands may be selected from but not limited to di-, tri-, and tetra-carboxylate ligands. For example, the carboxylate ligands may be 2',3'',5'',6'-tetramethyl-[1,1':4',1'':4'',1'''-quaterphenyl]3,3''', 5,5'''-tetracarboxylate, 1,3,5-benzenetribenzoate, and 4,4',4''-s-triazine-2,4,6-triyltribenzoate.

In a second aspect, the invention provides a method for preparing a metal organic framework comprising $Fe^{3+}$ or $Cr^{3+}$ ions and carboxylate ligands; the method comprising:
  reacting a metal organic framework comprising $M^{2+}$ metal ions and carboxylate ligands, wherein M is selected from Mg, Ca, Mn, Co, Ni, Cu, Zn, or Cd, with a source of $Fe^{2+}$ ions or $Cr^{2+}$ ions to provide a metal organic framework comprising $Fe^{2+}$ or $Cr^{2+}$ metal ions and carboxylate ligands; and
  exposing the metal organic framework comprising $Fe^{2+}$ or $Cr^{2+}$ metal ions to oxygen to provide a metal organic framework comprising $Fe^{3+}$ or $Cr^{3+}$ and carboxylate ligands.

The above method of the invention is referred to herein as Post-Synthetic Metathesis and Oxidation (PSMO). It takes advantage of the kinetically labile metal-ligand exchange reactions prior to oxidation, and the kinetically inert metal-ligand bonds after oxidation.

To date, there are approximately twenty examples of post-synthetic metal metathesis, and most of them occurred between two transition metals categorized as soft or borderline Lewis acids such as Mn(II), Co(II), Ni(II), Cu(II), Zn(II) and Cd(II). For example, see (a) Lalonde, M.; Bury, W.; Karagiaridi, O.; Brown, Z.; Hupp, J. T.; Farha, O. K. J. Mater. Chem. A. 2013, 1, 545. (b). Brozek, C. K.; Cozzolino, A. F.; Teat, S. J.; Chen, Y.-S. Dincă, M. Chem. Mater. 2013, 25, 2998. However, the success of these metal metatheses did not improve the stability of the MOFs because the resulting metal-ligand bonds were kinetically labile. Cohen and Dincă's groups have initially demonstrated the feasibility of post-synthetic exchange for normally "inert" frameworks or metal ions; see (a) Kim, M.; Cahill, J. F.; Fei, H.; Prather, K. A.; Cohen, S. M. J. Am. Chem. SOC. 2012, 134, 18082. (b) Brozek, C. K.; Dincă, M. J. Am. Chem. Soc. 2013, 135, 12886. However, attaining a complete metal exchange product can be a daunting task due to the inertness of the starting metal-ligand bonds. Moreover, earlier studies indicate that post-synthetic metal metathesis usually needs long duration ranging from a few days to several weeks. For example, see Lalonde, M.; Bury, W.; Karagiaridi, O.; Brown, Z.; Hupp, J. T.; Farha, O. K. J. Mater. Chem. A. 2013, 1, 545; Brozek, C. K.; Coz-zolino, A. F.; Teat, S. J.; Chen, Y.-S. Dinca, M. Chem. Mater. 2013, 25, 2998; Kim, M.; Cahill, J. F.; Fei, H.; Prather, K. A.; Cohen, S. M. J. Am. Chem. Soc. 2012, 134, 18082; Brozek, C. K.; Dincă, M. J. Am. Chem. Soc. 2013, 135, 12886; Dincă, M.; Long, J. R. J. Am. Chem. Soc. 2007, 129, 11172; and Kim, Y.; Das, S.; Bhattacharya, S.; Hong, S.; Kim, M. G.; Yoon, M.; Natarajan, S.; Kim. K. Chem. Eur. J. 2012, 18, 16642. In order to overcome the afore-mentioned challenges, it has been discovered that the following steps need to be taken: (1) selection of the template MOFs with labile metal-ligand bonds; (2) exchange with metal ions that can be oxidized to high oxidation state while preserving the coordination environment around metal ion.

The carboxylate ligands may be selected from any suitable carboxylate ligands. A range of suitable carboxylate ligands are provided below.

In particular, the carboxylate ligands may be selected from but not limited to di-, tri-, and tetra-carboxylate ligands. For example, the carboxylate ligands may be 2',3'',5'',6'-tetramethyl-[1,1':4',1'':4'',1'''-quaterphenyl]3,3''',5,5'''-tetracarboxylate, 1,3,5-benzenetribenzoate, and 4,4',4''-s-triazine-2,4,6-triyltribenzoate.

The metal organic framework comprising $M^{2+}$ metal ions employed in the method of the invention may be washed with organic solvent, such as DMF, before reacting with a source of $Fe^{2+}$ ions or $Cr^{2+}$ ions.

The step of reacting the metal organic framework comprising $M^{2+}$ metal ions with a source of $Fe^{2+}$ ions or $Cr^{2+}$ ions may be carried out in an inert atmosphere, e.g. under nitrogen.

The step of reacting the metal organic framework comprising $M^{2+}$ metal ions with a source $Fe^{2+}$ ions or $Cr^{2+}$ ions may be carried out from about 20 minutes to about 3 hours.

In the invention, the source of $Fe^{2+}$ ions may be any $Fe^{2+}$ salt. For example, the $Fe^{2+}$ salt may be a Fe(II) halide (such as $FeCl_2$) or a Fe(II) sulfate. Preferably, the $Fe^{2+}$ salt is an anhydrous salt. For example, the $Fe^{2+}$ salt may be an anhydrous Fe halide such as anhydrous $FeCl_2$. Likewise, the source of $Cr^{2+}$ ions may be any $Cr^{2+}$ salt. For example, the $Cr^{2+}$ salt may be a Cr(II) halide (such as $CrCl_2$) or a Cr(II)

sulfate. Preferably, the $Cr^{2+}$ salt is an anhydrous salt. For example, the $Cr^{2+}$ salt may be anhydrous Cr(II) sulphate or an anhydrous Cr(II) halide such as anhydrous $CrCl_2$.

In one embodiment of the method of the invention, the step of exposing the metal organic framework comprising $Fe^{2+}$ or $Cr^{2+}$ metal ions to oxygen comprises exposing the metal organic framework comprising $Fe^{2+}$ or $Cr^{2+}$ metal ions to an air stream.

In one embodiment of the method of the invention, the step of exposing the metal organic framework comprising $Fe^{2+}$ or $Cr^{2+}$ metal ions to oxygen further comprises suspending the metal organic framework comprising $Fe^{2+}$ or $Cr^{2+}$ metal ions in an organic solvent to provide a suspension. For example, the step of exposing the metal organic framework comprising $Fe^{2+}$ or $Cr^{2+}$ metal ions to oxygen may comprise suspending the metal organic framework comprising $Fe^{2+}$ or $Cr^{2+}$ metal ions in an organic solvent to provide a suspension and bubbling an air stream through the suspension. In the invention, the organic solvent may be any organic solvent. For example, the organic solvent may be DMF.

In one embodiment of the method of the invention, any excess of the source of $Fe^{2+}$ ions or $Cr^{2+}$ ions is removed before the metal organic framework comprising $Fe^{2+}$ or $Cr^{2+}$ metal ions is exposed to oxygen.

In a further aspect, the invention provides a method for preparing a metal organic framework comprising $Ti^{4+}$ ions and carboxylate ligands; the method comprising:

reacting a metal organic framework comprising $M^{2+}$ metal ions or $X^{3+}$ metal ions and carboxylate ligands, wherein M is selected from Mg, Ca, Mn, Co, Ni, Cu, Zn, or Cd, and X is selected from Sc, In or Ga, with a source of $Ti^{3+}$ ions to provide a metal organic framework comprising $Ti^{3+}$ metal ions and carboxylate ligands; and exposing the metal organic framework comprising $Ti^{3+}$ metal ions to oxygen to provide a metal organic framework comprising $Ti^{4+}$ and carboxylate ligands.

The above method is also a PSMO method.

The source of $Ti^{3+}$ ions may be any source of $Ti^{3+}$ ions. For example, the source of $Ti^{3+}$ ions may be selected from a Ti(III) halide or solvate thereof such as Ti(III) chloride or a solvate thereof, e.g. $TiCl_{3.3}THF$.

In one embodiment, the step of exposing the metal organic framework comprising $Ti^{3+}$ ions to oxygen comprises exposing the metal organic framework comprising $Ti^{3+}$ metal ions to an air stream.

In one embodiment, the step of exposing the metal organic framework comprising $Ti^{3+}$ metal ions to oxygen further comprises suspending the metal organic framework comprising $Ti^{3+}$ metal ions in an organic solvent to provide a suspension.

In one embodiment, the step of exposing the metal organic framework comprising $Ti^{3+}$ metal ions to oxygen comprises suspending the metal organic framework comprising $Ti^{3+}$ metal ions in an organic solvent to provide a suspension and bubbling an air stream through the suspension.

In one embodiment, the metal organic framework comprising $M^{2+}$ metal ions and carboxylate ligands is prepared by a method which comprises reacting a $M^{2+}$ metal salt hydrate with a carboxylic acid precursor of the carboxylate ligands.

In one embodiment, the metal organic framework comprising $X^{3+}$ metal ions and carboxylate ligands is prepared by a method which comprises reacting a $X^{3+}$ metal salt hydrate with a carboxylic acid precursor of the carboxylate ligands.

The $M^{2+}$ or $X^{3+}$ metal salt hydrate may be any $M^{2+}$ or $X^{3+}$ metal salt hydrate. Preferably, the $M^{2+}$ metal salt hydrate is $M(NO_3)^2.6H_2O$. Preferably, the $X^{3+}$ metal salt hydrate is $X(NO_3)^2.6H_2O$.

In the method of the present invention, the carboxylic acid may be any suitable carboxylic acid. Whichever carboxylic acid is employed, the resulting metal organic framework comprises the corresponding carboxylate ligands. Suitable carboxylate ligands are described herein in terms of the carboxylic acids from which they derive. These carboxylic acids can therefore be employed in this aspect of the invention. For example, for illustrative purposes only, when 2',3'',5'',6'-tetramethyl-[1,1':4',1'':4'',1'''-quaterphenyl]3,3''', 5,5'''-tetracarboxylic acid is used, the resulting metal organic framework comprises 2',3'',5'',6'-tetramethyl-[1,1':4',1'':4'', 1'''-quaterphenyl]3,3''',5,5'''-tetracarboxylate ligands.

Regarding the final product of the method of the invention, the metal organic framework comprising $Fe^{3+}$ or $Cr^{3+}$ metal ions may have an Fm-3m crystal space group.

Regarding the final product of the method of the invention, the metal organic framework comprising $Fe^{3+}$ or $Cr^{3+}$ metal ions may be octahedrally coordinated with three $Fe^{3+}$ or $Cr^{3+}$ metal ions sharing a common oxygen to form a $[Fe/Cr_3(\mu-O)]$ cluster. In particular, each $[Fe/Cr(\mu-O)]$ cluster may be connected with four carboxylate ligands and four aqua ligands.

Regarding the final product of any method of the invention, the carboxylate ligands may be any suitable carboxylate ligand such as a carboxylate ligand derived from a carboxylic acid as described above. For example, the ligands may be di-, tri-, or tetra-carboxylate ligands. In particular, the ligands may be tetra-carboxylate ligands such as 2',3'', 5'',6'-tetramethyl-[1,1':4',1'':4'',1'''-quaterphenyl]3,3''',5,5'''-tetracarboxylate ligands.

As stated above, the present invention also provides metal organic frameworks comprising $Cr^{3+}$ ions in a monocrystalline form for the first time.

In a further aspect, the invention provides a monocrystalline metal organic framework comprising $Ti^{4+}$, $Fe^{3+}$ or $Cr^{3+}$ ions and carboxylate ligands obtained/obtainable by a method of the invention described above.

An alternative method for preparing Cr(III)-MOFs has also been developed by the present inventors. It has been discovered that Fe(III)-MOFs could be feasible structural templates for the construction of Cr(III)-MOFs because iron resembles chromium in both coordination geometry and valence. More importantly, the single crystalline samples can be readily achievable for Fe-MOFs, which greatly facilitate the structural characterization of the exchanged product. However, complete metathesis of Fe by Cr is usually hampered by the thermodynamic stability of iron-ligand coordination bond. Herein, we report a novel reductive labilization-metal metathesis route for the construction of ultrastable mesoporous Cr(III)-MOFs from a robust iron template, wherein redox chemistry has contributed to the generation of labile metathesis intermediates. This metathesis has resulted in the generation of a chemically more robust mesoMOF due to the kinetic inertness of Cr(III). The method is a post-synthetic reduction metathesis and oxidation (PSRMO).

The invention therefore also provides a further method for preparing metal organic frameworks comprising $Cr^{3+}$ ions, preferably in monocrystalline form, for the first time.

Accordingly, the invention provides a method for preparing a metal organic framework comprising $Cr^{3+}$ ions; the method comprising:

reacting a metal organic framework comprising $X^{3+}$ ions, wherein X is selected from Fe, Sc, In or Ga, and carboxylate ligands with a source of $Cr^{2+}$ ions to provide a metal organic framework comprising $Cr^{2+}$ ions and carboxylate ligands; and exposing the metal organic framework comprising $Cr^{2+}$ ions and carboxylate ligands to oxygen to provide the metal organic framework comprising $Cr^{3+}$ ions and carboxylate ligands.

The step of reacting the metal organic framework comprising $X^{3+}$ ions and carboxylate ligands with the source of $Cr^{2+}$ ions comprises a step of reducing the metal organic framework comprising $X^{3+}$ ions to a metal organic framework comprising $X^{2+}$ ions and then a metal metathesis step replacing the $X^{2+}$ ions with $Cr^{2+}$ ions. It is therefore seen that the $Cr^{2+}$ ions are responsible for both the reduction step and the metal metathesis step.

In one embodiment, the $X^{3+}$ ions are $Fe^{3+}$ ions.

In the method, $X^{3+}/Fe^{3+}$ in the starting metal organic framework is reduced to $X^{2+}/Fe^{2+}$ by $Cr^{2+}$. Subsequently, $X^{2+}/Fe^{2+}$ is exchanged by $Cr^{2+}$, which proceeds to oxidize to $Cr^{3+}$ in the presence of oxygen.

In this method of the invention, the metal organic framework comprising $Fe^{3+}$ ions and carboxylate ligands may include only $Fe^{3+}$ ions or may include a metal cation mixture of $Fe^{3+}$ and $X^{2+}$ ions; wherein X is a metal ion selected from the group consisting of Group 2 through Group 16 metals. For example, X may be a metal ion selected from Al(III), Fe(II,III), Co(II), Ni(II), Mn(II), Zn(II), Mg(II), Cr(III), V(III), Sc(III), Ca(II), Ba(II) or In(III), preferably X is a metal ion selected from Fe(II,III), Co(II), Ni(II), Mn(II), Zn(II), and Mg(II).

The source of $Cr^{2+}$ ions may be any suitable Cr salt including but not limited to chromium sulfates and chromium halides such as $CrCl_2$.

The carboxylate ligands may be selected from any suitable carboxylate ligands. A range of suitable carboxylate ligands are provided below.

In particular, the carboxylate ligands may be selected from but not limited to di-, tri-, and tetra-carboxylate ligands. For example, the carboxylate ligands may be 2',3'',5'',6'-tetramethyl-[1,1':4',1'':4'',1'''-quaterphenyl]3,3''',5,5'''-tetracarboxylate, 1,3,5-benzenetribenzoate, and 4,4',4''-s-triazine-2,4,6-triyltribenzoate.

The method may be carried out in DMF.

The methods described herein allow single crystal to single crystal transformation providing a potential way of obtaining new monocrystalline metal organic frameworks comprising $Ti^{4+}$, $Fe^{3+}$ or $Cr^{3+}$ ions. The method also allows polycrystalline to polycrystalline transformation providing a potential way of obtaining new polycrystalline metal organic frameworks comprising $Ti^{4+}$, $Fe^{3+}$ or $Cr^{3+}$ ions.

Accordingly, the methods may be employed to prepare a monocrystalline metal organic framework comprising $Cr^{3+}$ ions and carboxylate ligands, wherein the metal organic framework comprising $Fe^{3+}$ ions, i.e. the precursor to the Cr-MOF, is monocrystalline.

Alternatively, the methods may be employed to prepare a polycrystalline metal organic framework comprising $Cr^{3+}$ ions, i.e. the precursor to the Cr-MOF, and carboxylate ligands, wherein the metal organic framework comprising $Fe^{3+}$ ions is polycrystalline.

In a further aspect, the invention provides a monocrystalline metal organic framework comprising $Cr^{3+}$ ions and carboxylate ligands obtained/obtainable by this method.

In a further aspect, the invention provides a metal organic framework comprising $Mg^{2+}$ ions and carboxylate ligands. Such a metal organic framework may be employed as a reactant (i.e. a MOF comprising $M^{2+}$ ions and carboxylate ligands) in one of the method described above. Such a MOF has not been described in the literature to date.

Accordingly, the invention provides a metal organic framework comprising $Mg^{2+}$ metal ions and carboxylate ligands, wherein each $Mg^{2+}$ metal ion is octahedrally coordinated and in which three $Mg^{2+}$ metal ions share a common oxygen to form a $[Mg_3(\mu-O)]$ cluster, each cluster is coordinated with four carboxylate ligands and four aqua ligands.

In particular, the carboxylate ligands are 2',3'',5'',6'-tetramethyl-[1,1':4',1'':4'',1'''-quaterphenyl]3,3''',5,5'''-tetracarboxylate ligands.

In a further aspect, the invention provides a method for preparing such a metal organic framework. That is the invention provides a method for preparing a metal organic framework comprising $Mg^{2+}$ metal ions and carboxylate ligands, the method comprising reacting a $Mg^{2+}$ metal salt hydrate with a carboxylic acid precursor of the carboxylate ligands.

In one embodiment, the carboxylic acid precursor is 2',3'',5'',6'-tetramethyl-[1,1':4',1'':4'',1'''-quaterphenyl]3,3''',5,5'''-tetracarboxylic acid.

In a further aspect, the invention provides the use of a metal organic framework comprising $Mg^{2+}$ metal ions and carboxylate ligands, wherein each $Mg^{2+}$ metal ion is octahedrally coordinated and in which three $Mg^{2+}$ metal ions share a common oxygen to form a $[Mg_3(\mu-O)]$ cluster, each cluster is coordinated with four carboxylate ligands and four aqua ligands, in the preparation of a monocrystalline metal organic framework comprising $M^{3+}$ ions and carboxylate ligands, wherein M is Fe or Cr.

The metal-organic frameworks according to the invention have a wide range of applications.

According to one aspect, the invention provides a method comprising uptaking at least one substance by a metal-organic framework of the present invention.

For example, the substance may be hydrogen, methane, oxygen, carbon dioxide or nitrogen.

According to one aspect, the invention provides a method of storing a gas in a metal-organic framework according to the present invention. Alternatively, the invention provides the use of a metal-organic framework according to any embodiment of the present invention for storing a gas. This may be achieved by binding the gas in a plurality of linker channel sites present in the metal-organic framework, for example using van der Waals forces.

The use/method of storing gases in this way may optimise gas storage density and volumetric gas storage.

For example, the gas may be hydrogen, methane, oxygen, carbon dioxide or nitrogen.

In the above embodiments of the invention, the metal-organic framework may be configured to store methane or hydrogen, for example for fuelling vehicles.

In a further aspect, the present invention provides the use of any metal-organic framework according to the invention for adsorbing a guest molecule, for example a gas molecule such as hydrogen, methane, oxygen, carbon dioxide or nitrogen. In this respect, the invention also provides a method of adsorbing a guest molecule, for example a gas molecule such as hydrogen, methane, oxygen, carbon dioxide or nitrogen, comprising contacting a metal-organic framework of the invention with a guest molecule source.

Accordingly, the invention also provides a metal-organic framework according to any embodiment of the present invention, further comprising one or more than one type of guest molecule.

The guest molecule may be a gas molecule such as hydrogen, methane, oxygen, carbon dioxide or nitrogen.

In fact, in the context of any of the embodiments described herein, the substance, gas molecule, or gas may be selected from:

(a) $H_2$, $N_2$, Ar, $O_2$, $CO_2$, NO, $NO_2$ or CO; or
(b) an alkane (C1-6), alkene (C2-4), alkyne (C2-6), alcohol (C1-6), arene (C6-8) or a substituted version of any of these;
wherein the alkane may be selected from $CH_4$, $C2H_6$, $C_3H_8$, $C_4H_{10}$, $C_5H_{12}$ or $C_6H_{14}$; or a cycloalkane (C3-6) selected from the group consisting of $C_3H_6$, $C_4H_8$, $C_5H_{10}$ and $C_6H_{14}$;
wherein the alkene may be $C_2H_4$, $C_3H_6$, $C_4H_8$, $C_5H_{10}$ or $C_6H_{12}$;
wherein the alkyne may be $C_2H_2$;
wherein the alcohol may be methanol, ethanol, n-propanol, isopropanol, n-butanol or isobutanol; or
wherein the arene may be a substituted arene (C6-8) such as is nitrobenzene, 1,2-dinitrobenzene, 1,3-dinitrobenzene, 1,4-dinitrobenzene, 1,2,4-trinitrobenzene or 1,3,5-trinitrobenzene.

DESCRIPTION OF THE FIGURES

The invention will now be described further with reference to the following non-limiting examples and the accompanying Figures, in which.

Figure 15:
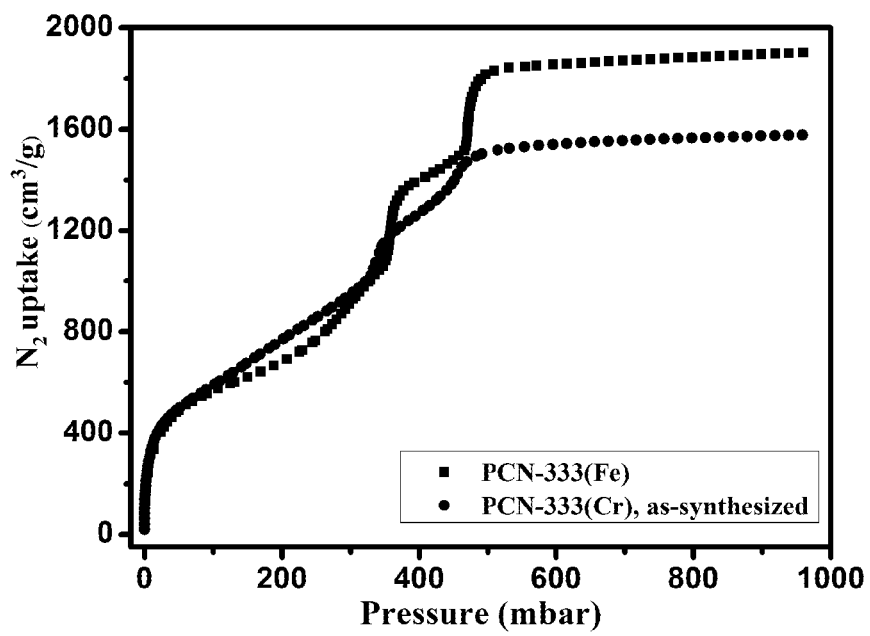
FIG. 15 shows the $N_2$ adsorption isotherm of PCN-333-Cr(III) and PCN-333-Fe.

A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. A polycrystalline solid or polycrystal is comprised of many individual grains or crystallites. There is no relationship between the grains. Therefore, on a large enough length scale, there is no periodicity across a polycrystalline sample. They are different from monocrystalline materials. Large single crystals are very rare in nature and can be difficult to produce in the laboratory. It is desired that metal organic framework materials should be free from objectionable or incompatible impurities which detrimentally affect the crystal structure or the physical properties of the crystal. The material should be finely divided and uniform in size. Due to the absence of the defects associated with grain boundaries, monocrystalline metal organic frameworks have high surface areas and provide control over the crystallization process. The differences between amorphous, polycrystalline and (mono)crystalline are illustrated in FIG. 15.

In preferred embodiments of the invention, the monocrystalline metal organic frameworks comprise a low occurrence of twinning. For example, the monocrystalline metal organic frameworks may comprise less than about 5% twinning crystals. Most preferred, the monocrystalline metal organic frameworks comprise no twinning crystals.

In all these embodiments, the crystal size may be measured as the largest dimension of a single crystal. For example, the largest dimension of a single crystal as measured under an (optical) microscope.

Carboxylate ligands are employed in the various aspects of the present invention.

The carboxylate ligands may be any suitable carboxylate ligand including but not limited to ligands having two or more carboxylate groups. For example, the carboxylate ligands may be derived from a dicarboxylic acid, a tricarboxylic acid, a tetracarboxylic acid, a hexcarboxylic acid or an octacarboxylic acid For the purposes of the present invention, the term "derived" means that the carboxylic acid compounds are present in partly deprotonated or fully deprotonated form.

For example, a ligand may be derived from a dicarboxylic acid, such as, for instance, oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzene-dicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzene-dicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclo-hexadiene-1,2-dicarboxylic acid, octanedicarboxylic acid, pentane-3,3-dicarboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-binaphthyidicarboxylic acid, 7-chloro-8-methylquinoline-2,3-dicarboxylic acid, 1-anilinoanthraquinone-2,4'-dicarboxylic acid, poly-tetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro) phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazine-dicarboxylic acid, 4,4'-diamino (diphenylether)diimidedicarboxylic acid, 4,4'-diaminodiphenylmethanediimidedicarboxylic acid, 4,4'-diamino(diphenyl sulfone)diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4"-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptane-dicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxy-diphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitro-benzene-1,4-dicarboxylic acid, heptane-1,7-dicarboxylic acid, cyclobutane-1,1-dicarboxylic acid, 1,14-tetradecanedicarboxylic acid, 5,6-dehydronorbomane-2,3-dicarboxylic acid, 5-ethyl-2,3-pyridinedicarboxylic acid or camphordicarboxylic acid.

For example, a ligand may be derived from a tricarboxylic acid, such as for instance 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

For example, a ligand may be derived from a tricarboxylic acid, such as for instance 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

For example, a ligand may be derived from a tetracarboxylic acid, such as, for instance, 1,1-dioxidoperylo[1,12-BCD]thiophene-3,4,9,10-tetracarboxylic acid, perylene-tetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octane-tetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.
The ligands may also be derived from a carboxylic acid selected from compounds of formula L1 to L30 and combinations thereof:
L1
L2
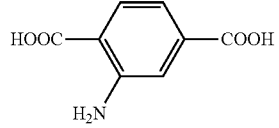
L3
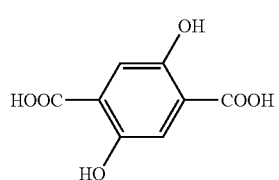
L4
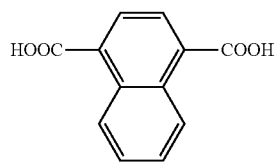
L5
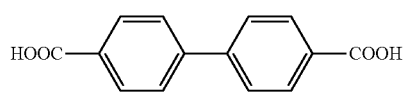
L6
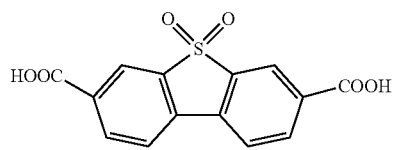
L7
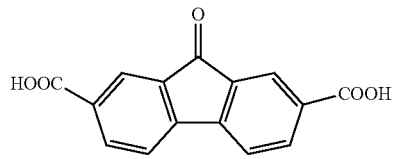
L8
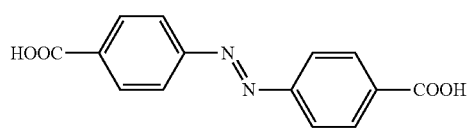
L9
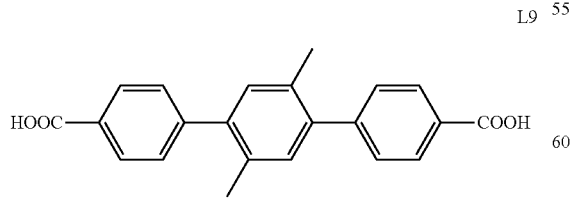
L10
-continued
L11
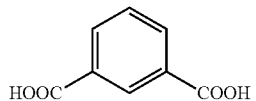
L12
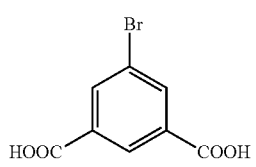
L13
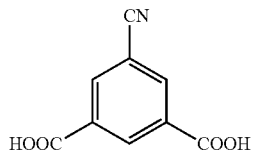
L14
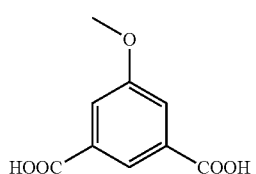
L15
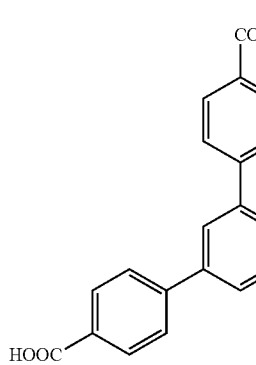
L16
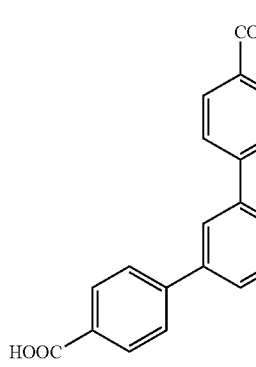

L17
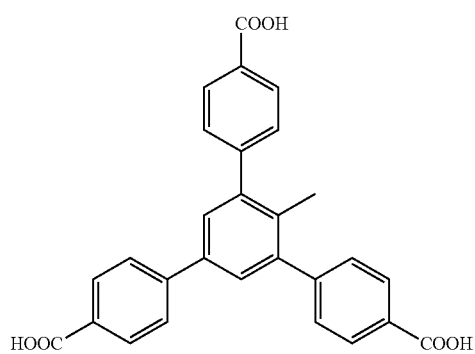
L18
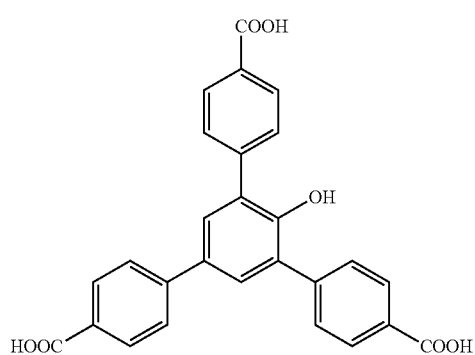
L19
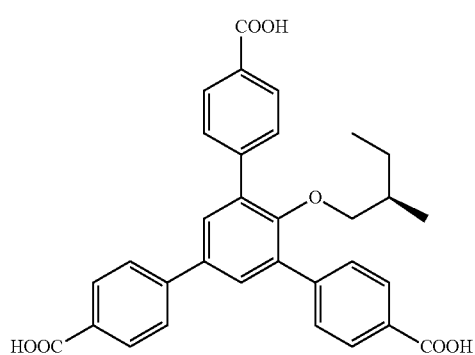
L20
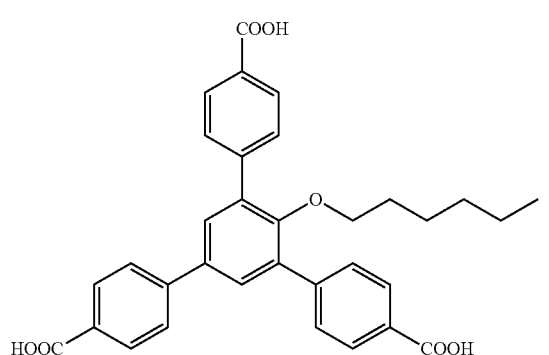
L21
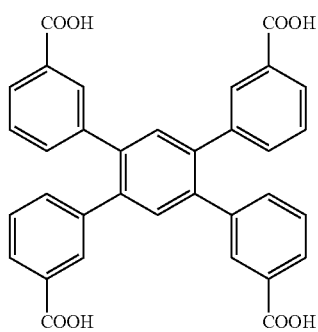
L22
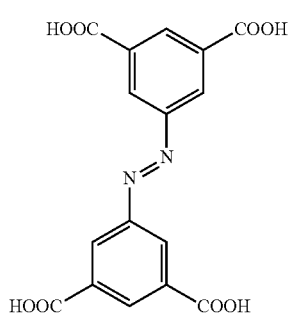
L23
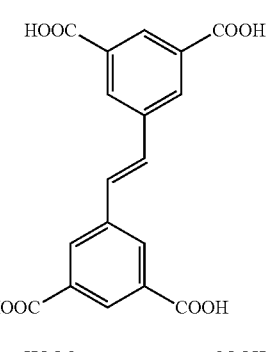
L24
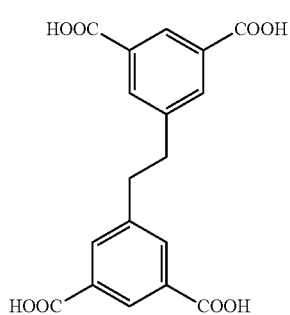
L25
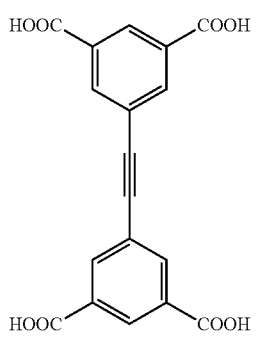

L26
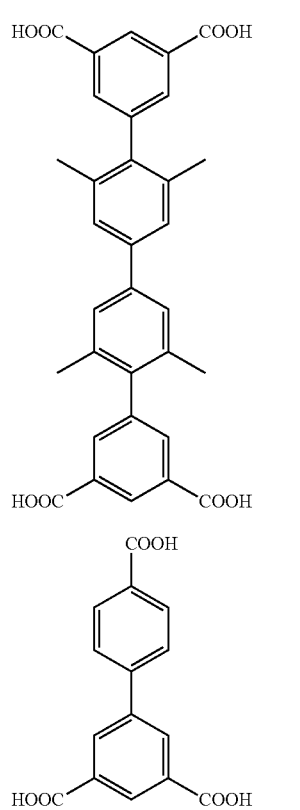
L27
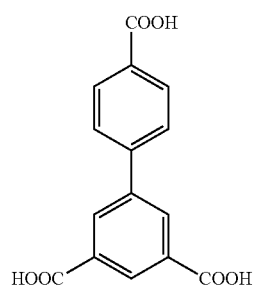
L28
L29
L30
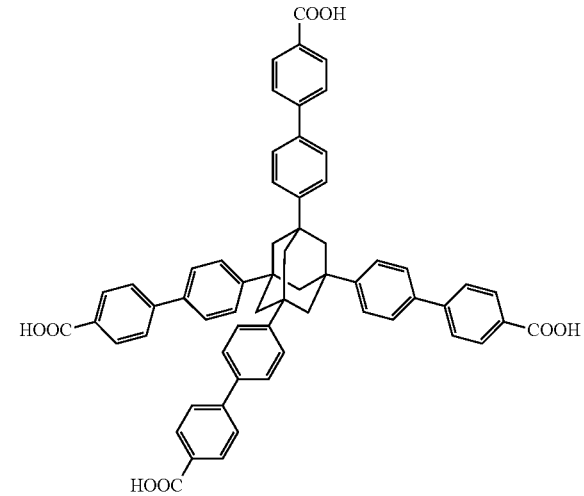
Specific combinations of ligands include ligands derived from L31 and L32:
L31
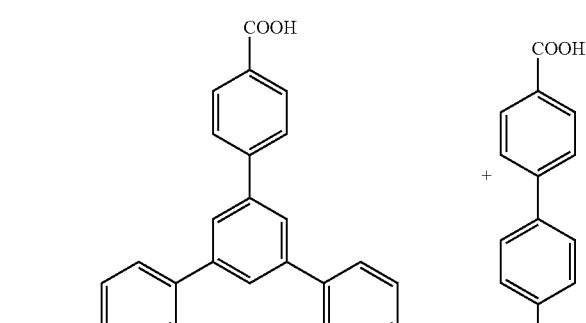
L32
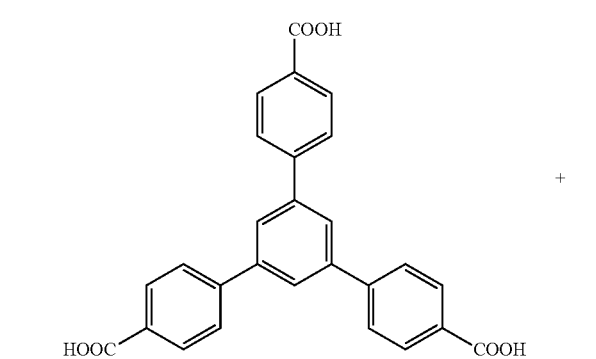

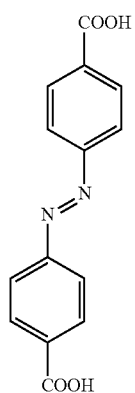
Alternatively, the ligand may be derived from a carboxylic acid selected from the following compounds or combinations thereof:
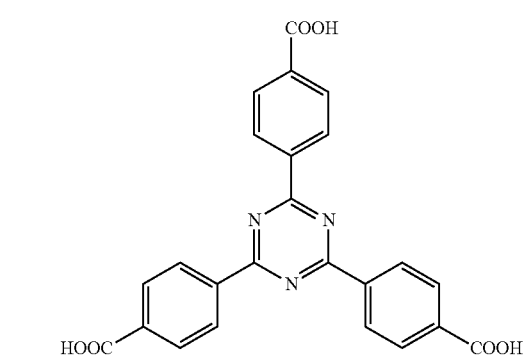
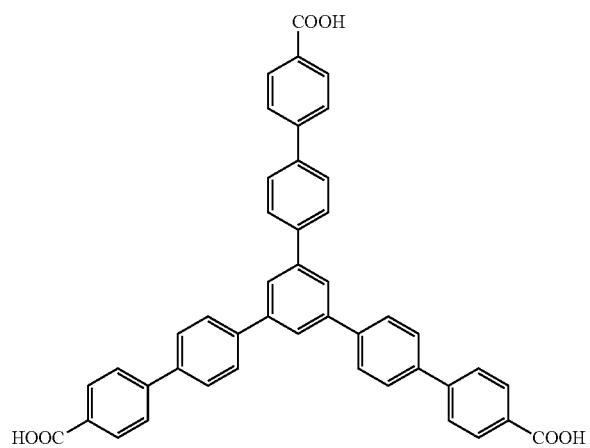
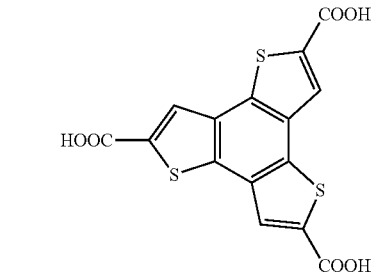
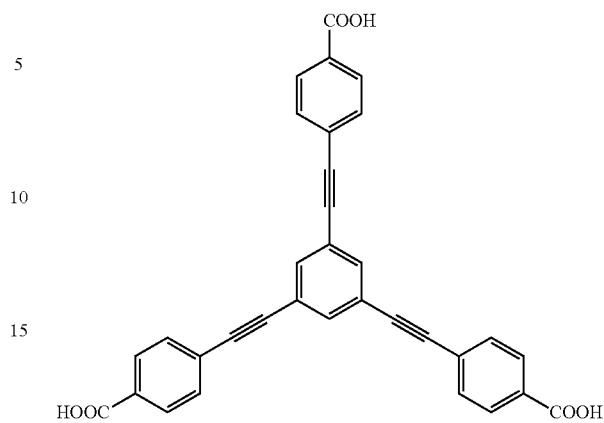
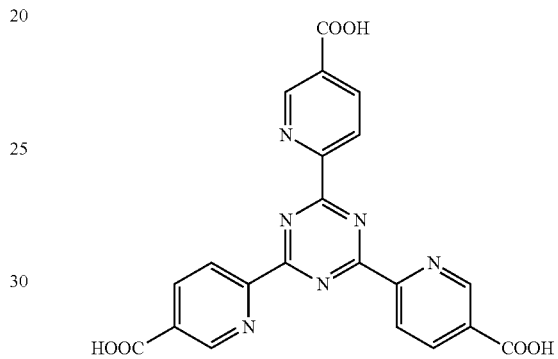
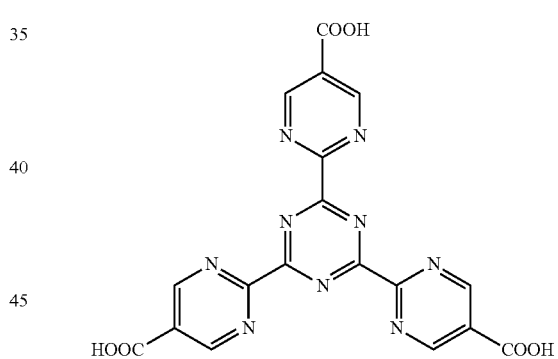
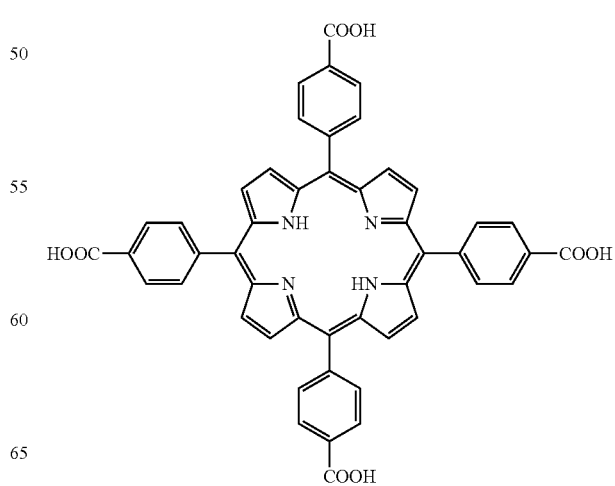

-continued

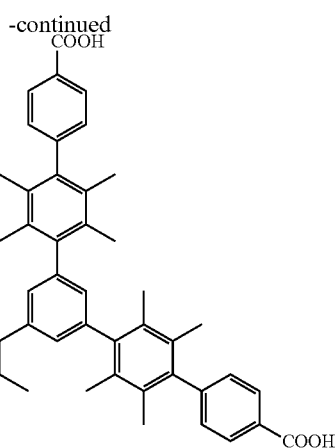

In the invention, the carboxylate ligands may be selected from but not limited to di-, tri-, and tetra-carboxylate ligands. For example, the carboxylate ligands may be derived from 2',3",5",6'-tetramethyl-[1,1':4',1":4",1"'-quaterphenyl]3,3"',5,5"'-tetracarboxylic acid, 1,3,5-benzenetribenzoic acid, or 4,4',4"-s-triazine-2,4,6-triyltribenzoic acid.

2',3",5",6'-tetramethyl-[1,1':4',1":4",1"'-quaterphenyl]3,3"',5,5"'-tetracarboxylic acid has chemical structure:

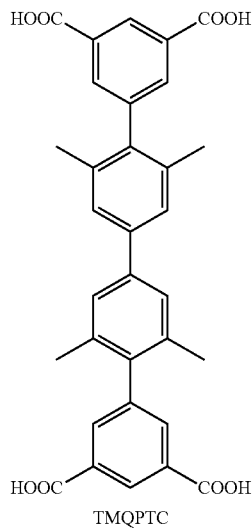 [SMILES: Cc1cc(-c2cc(C)c(-c3cc(C(=O)O)cc(C(=O)O)c3)c(C)c2)cc(C)c1-c1cc(C(=O)O)cc(C(=O)O)c1]

TMQPTC 1,3,5-benzenetribenzoic acid has the chemical structure:

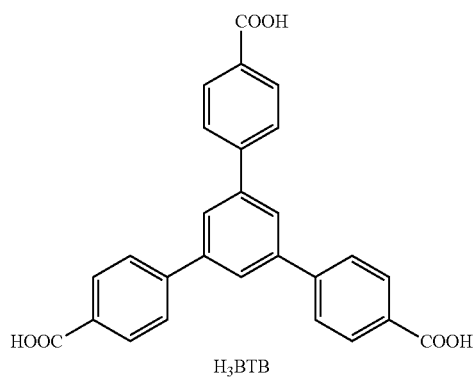

H₃BTB 4,4',4"-s-triazine-2,4,6-triyltribenzoic acid has the chemical structure:

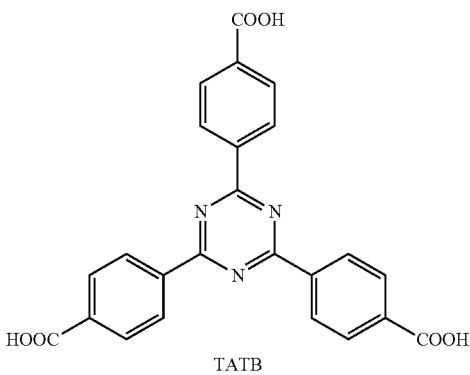

TATB

In one embodiment, the ligands are derived from a carboxylic selected from L3, L9, L15, L16, L17, L18, TMQPTC, H₃BTB, and BTC.

The present invention is described in more detail below in the context of specific examples. However, the invention should not be construed so as to be limited by these specific examples.

PSMO

We synthesized Mg-MOF (denoted as PCN-426-Mg, PCN stands for Porous Coordination Network) as a framework template wherein the Mg—O bond is more labile than common coordination bonds. Crystallographic studies revealed that the Mg atoms in PCN-426-Mg form the oxo-trinuclear cluster usually observed in both iron and chromium chemistry; this illustrated in FIG. 1. For example, also see (a) Serre, C.; Mellot-Draznieks, C.; Surblé, S.; Audebrand, N.; Filinchuk, Y.; Ferey, G. Science 2007, 315, 1828. (b) Tranchemontagne, D. J.; Mendoza-Cortes, J. L.; O'Keeffe, M.; Yaghi, O. M. Chem. Soc. Rev. 2009, 38, 1257. This leads to the possibility of applying PSMO strategy to obtain MOFs of Fe(III) and Cr(III) with Mg(II)-MOF as template. To accelerate the exchange rate and to preserve the overall structure, we first use $Fe^{2+}$ and $Cr^{2+}$ to form the intermediate Fe(II) and Cr(II)-MOFs. After air oxidation, ultra water-stable MOFs, PCN-426-Fe(III) and PCN-426-Cr(III), were obtained in a Single Crystal to Single Crystal (SC-SC) transformation following a procedure such as those set out in (a) Halder, G. J.; Kepert, C. J. Aust. J. Chem. 2006, 59. 597; and (b) MacGillivray, L. R.; Papaefstathiou, G. S.; Friščićs, T.; Hamilton, T. D.; Bučar, D.-K.; Chu, Q.; Varshney, D. B.; Georgiev, I. G. Acc. Chem. Res., 2008, 41, 280; the contents of which are hereby incorporated in its entirety. Significantly, these MOFs that contain high-valence metals, especially Cr(III), were made almost exclusively in the form of crystalline powders until this work; see (a) Férey, G.; Mellot-Draznieks, C.; Serre, C.; Millange, F.; Dutour, J.; SurbléS.; Margiolaki, I. Science, 2005, 309, 2040. (b) Férey, G.; Serre, C.; Mellot-Draznieks, C.; Millange, F.; Surblé, S.; Dutour, J.; Margiolaki, I. Angew. Chem. Int. Ed. 2004, 43, 6296. (c). Serre, C.; Millange, F.; Thouvenot, C.; Noguës, M.; Marsolier, G.; Louër, D.; Ferey, G. J. Am. Chem. Soc. 2002, 124, 13519; the contents of which are hereby incorporated in its entirety. In contrast, the present invention provides metal organic frameworks in monocrystalline form.

The colorless crystal of PCN-426-Mg was synthesized by a solvothermal reaction of Mg(NO₃)₂.6H₂O, and TMQPTC (2',3''',5'',6'-tetramethyl-[1,1':4',1'':4'',1'''-quaterphenyl]3,3''', 5,5'''-tetracarboxylic acid) at 100° C. for 24 hours. X-ray diffraction study reveals that PCN-426-Mg crystalizes in Fm-3m space group. Each Mg(II) is octahedrally coordinated with three of them sharing a common oxygen to form a [$M_3(\mu_3$-O)] cluster.

Further inspection of the structure of PCN-426-Mg reveals that each cluster is connected with four carboxylate ligands with the remaining four coordination sites occupied by aqua ligands. This is quite different from previously reported [$M_3(\mu_3$-O)] clusters, which are usually fully coordinated by carboxylates, giving rise to six connected inorganic nodes. The reduced connectivity of the inorganic nodes and increased number of terminal aqua ligands not only allow easy access for the incoming metal ions during metal-ion exchange but also stabilize the overall framework throughout the metathesis. Furthermore, the [$M_3(\mu_3$-O)] cluster can accommodate both divalent and trivalent metal ions by varying charges on the terminal ligands, the bridging O atom, and/or the counter ions. This allows the incorporation of both divalent and trivalent metal ions in PCN-426-M with the original framework structure preserved. Due to its excellent stability, PCN-426-M(III) is the desired product, which the inventors have identified can be obtained through two conceivable routes: direct metathesis or PSMO. In the following, direct metathesis is shown as an experimental control to PSMO.

After a direct metal metathesis of PCN-426-Mg with anhydrous $FeCl_3$ in DMF for 12 hours, the crystal changed from colorless to red and became opaque. However, following a direct metal metathesis of PCN-426-Mg with $CrCl_3$ under similar reaction conditions, there was only a slight color change occurred. Energy-dispersive X-ray spectroscopy (EDS) studies revealed that 87% of Fe and only trace amount of Cr were exchanged. The metal exchange procedure includes Mg—O bond dissociation and M-O (M=Fe, Cr) bond formation, which is similar to a ligand exchange process in that both are based on the bonding strength of M-O bonds. Although the exchange rate of a specific metal ion differs for ligands, the comparison of their water exchange rate can be used to gauge the relative reactivity of two metal ions in post-synthetic exchange. For $Fe^{3+}$, the ligand exchange reaction rate constant is around $10^2$ (k, $sec^{-1}$). For $Cr^{3+}$, the kinetically inert $d^3$ configuration results in a much slower reaction rate constant of $10^{-6}$ (k, $sec^{-1}$).[11] Consequently, even after a long period of time, only part of the $Mg^{2+}$ ions in the inorganic nodes can be exchanged in PCN-426-Mg using $M^{3+}$ ($Cr^{3+}$ and $Fe^{3+}$) ions, although the $Fe^{3+}$ exchange reaction understandably went much further than that of $Cr^{3+}$.

In addition to the incomplete metal exchange, PXRD pattern indicates framework decomposition after $Mg^{2+}/Fe^{3+}$ exchange. Since $Fe^{3+}$ and $Cr^{3+}$ are both harder lewis acidic species compared to $Mg^{2+}$, they can competitively bond to the carboxylates and that would damage the skeleton of template MOF. Meanwhile, these hard lewis acidic species can undergo hydrolysis during the metal metathesis due to the adventitious water in the template framework. To test this hypothesis, we conducted the previous metal metathesis reactions using $Fe(NO_3)_3 \cdot 6H_2O$ and $Cr(NO_3)_3 \cdot 6H_2O$ instead of anhydrous $FeCl_3$ and $CrCl_3$ to intentionally introduce water molecules. With $Fe(NO_3)_3 \cdot 6H_2O$, the color of the crystal changed to red followed by decomposition of the framework and the appearance of a white precipitate in 12 hours. For $Cr(NO_3)_3 \cdot 6H_2O$, the PCN-426-Mg crystal was completely decomposed to form a homogenous solution. The hydrolysis equilibrium constant of $Fe^{3+}$ and $Cr^{3+}$ ($pK_a=2.2$ and 4 respectively) is much larger than that of $Fe^{2+}$ and $Cr^{2+}$ ($pK_a=9.5$ and 10 respectively) creating a higher aqueous proton concentration in the metal metathesis reaction; see (a) Baes, C. F.; Mesmer, R. E.; The Hydrolysis of Cations, Wiley-Interscience, New York, 1976. (b) Burgess, J. Metal Ions in Solutions, Ellis Horwood, Chichester, England, 1978, 264. An acidic environment is detrimental to the fragile Mg—O bond and induces the decomposition of the framework. Moreover, the loss of crystallinity can greatly impair the diffusion of metal ions, which hampers further metal exchange, leading to incomplete metathesis. This control experiment has exposed the disadvantage of direct metal-metathesis with $M^{3+}$ species: (1) $Fe^{3+}$ and $Cr^{3+}$ have very low ligand exchange rate and display kinetic inertness; and (2) larger hydrolysis equilibrium constants produce more acidic environment destroying the integrity of the MOF.

In conclusion, we have discovered that direct metal metathesis of $Mg^{2+}/Fe^{3+}$ or $Mg^{2+}/Cr^{3+}$ is not a viable synthetic route toward stable high-valence MOFs. In contrast, the present invention represents a stepwise synthesis of MOFs via Post-Synthetic Metathesis with low-valence metal ions and followed by the Oxidation of metal nodes. First, the as-synthesized PCN-426-Mg crystals were washed with dry DMF several times and bubbled with nitrogen for 15 min, and anhydrous $FeCl_2$ was added under the protection of nitrogen. This resulted in an evident color change of the crystals from colorless to purple in merely 20 minutes with complete exchange after 3 hours. After the removal of the excess $FeCl_2$ solution with a syringe, the solid was washed with fresh DMF to yield light brown crystals. The sample was suspended in an aliquot of DMF and bubbled with an air stream for 15 minutes, causing an apparent color change of the crystal to dark brown. Single crystal X-ray diffraction (Table 1), X-ray photoelectron spectroscopy and EDS spectrum (Table 2) have confirmed that the PSMO procedure was accomplished in a SC-SC transformation to give PCN-426-Fe(III).

PCN-426-Cr(III) was synthesized through the same PSMO method using anhydrous $CrCl_2$, yielding an even more evident color change from colorless to brown after metathesis and finally to dark blue upon oxidation. Single crystal X-ray crystallographic studies indicate that these new MOFs are isostructural with the Mg-MOF template. The successful synthesis of PCN-426-Fe(III) and PCN-426-Cr(III) illustrate the dominant advantages of PSMO: (1) the stepwise strategy make the metal metathesis much faster and more complete. Without being bound by theory, it is proposed that the primary advantage is on account of the substantial improvement in ligand exchange rates, which is an up to $10^5$ fold increase from $Fe^{3+}$ ($10^2$ (k, $sec^{-1}$)) to $Fe^{2+}$ (107 (k, $sec^{-1}$)) and an as large as $10^{16}$ fold improvement from $Cr^{3+}$ ($10^{-6}$ (k, $sec^{-1}$)) to $Cr^{2+}$ ($10^{10}$ (k, $sec^{-1}$)) due to the electron configuration changes from $d^3$ to $d^4$. PSMO also alleviates the challenges of partial exchange and kinetic inertness. (2) $Fe^{2+}$ and $Cr^{2+}$ are softer Lewis acids, which interact more weakly with carboxylate ligand (a hard Lewis base) than hard Lewis acids such as $Fe^{3+}$ and $Cr^{3+}$, so the metal metathesis can be conducted with less destruction of crystallinity. (3) Metal ions with smaller hydrolysis equilibrium constants provide a relative milder condition where the framework template remains intact during the exchange and facilitates the transportation of metal ions toward metal exchange completion. (4). The subsequent air oxidation is a very gentle but effective post-synthetic treatment.

Figure 1:
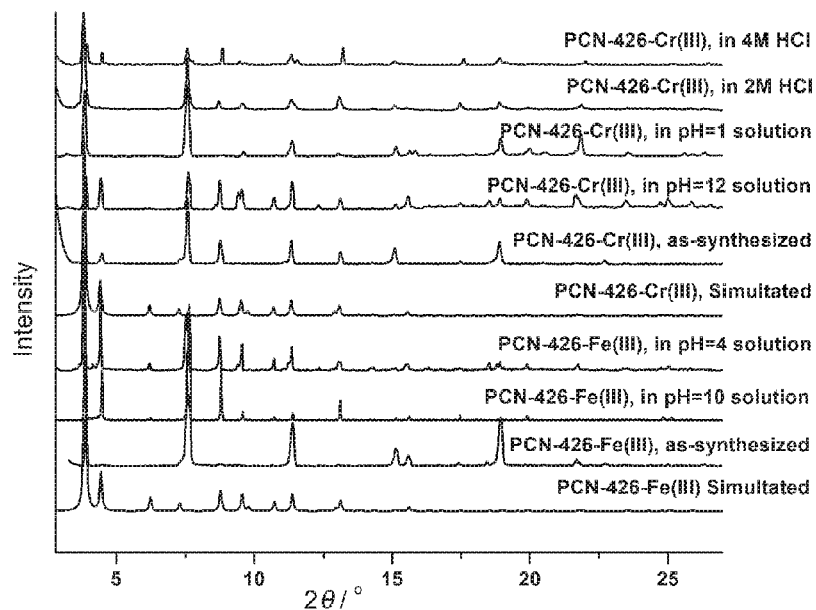
FIG. 1 shows the PXRD patterns of as-synthesized PCN-426-Mg, PCN-426-Fe(M), and PCN-426-Cr(III) as well as samples treated with a variety of aqueous solutions.
Figure 2:
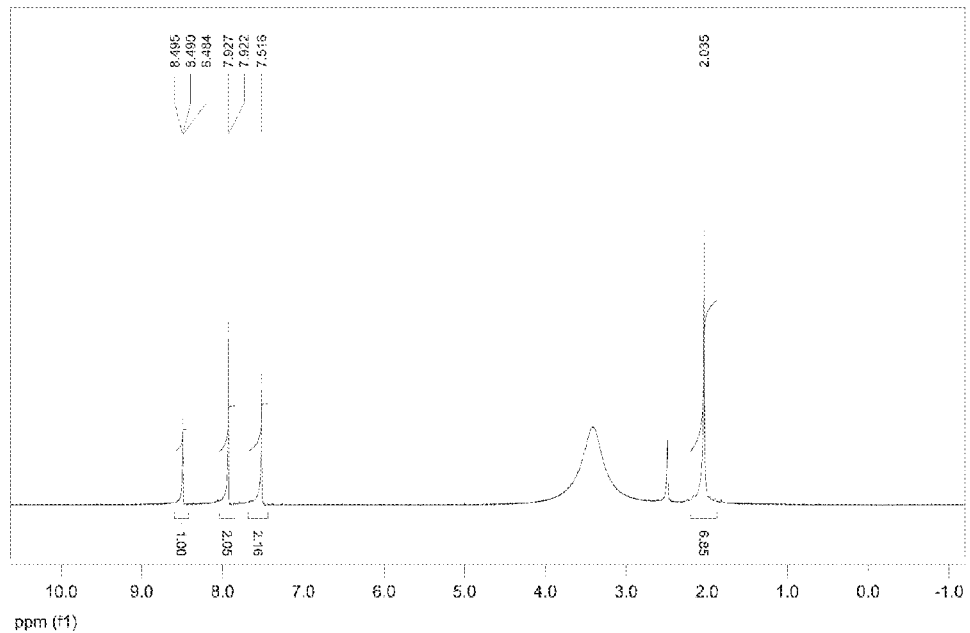
FIG. 2 shows the NMR spectrum of ligand TMQPTC.
Figure 5:
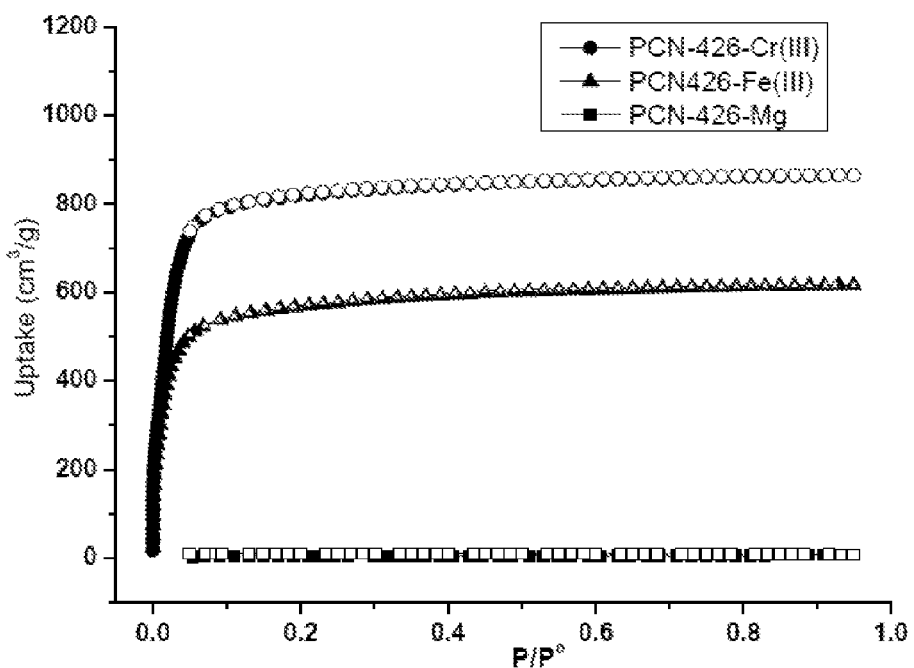
FIG. 5 shows the $N_2$ adsorption isotherms of PCN-426-Mg, PCN-426-Fe(III) and PCN-426-Cr(III).

After the labile Mg—O bonds have been replaced by inert Fe—O and Cr—O bonds, the stability of frameworks was greatly improved. For example, PCN-426-Mg was dissolved immediately after immersion in water, while PCN-426-Fe (III) is stable in water after one day. PXRD patterns confirm the framework is stable in aqueous solutions with pH values from 4 to 10 (FIG. 1). Although Cr(III) has the same valence and similar radius with Fe(III), the kinetic inertness has induced a stability of PCN-426-Cr(III) higher than that of PCN-426-Fe(III). PXRD studies indicated that the crystallinity of PCN-426-Cr(III) remains intact from pH=12 to extremely acidic conditions (4M HCl) for at least 12 h (FIG. 1). Benefiting from the improved stability, both PCN-426-Fe(III) and PCN-426-Cr(III) exhibit permanent porosity whereas PCN-426-Mg does not as shown by $N_2$ adsorption isotherms (FIG. 5). A Brunauer-Emmett-Teller (BET) surface area of 1770 and 3193 $m^2/g$ (Langmuir surface area of 2623 and 3883 $m^2/g$) were observed for PCN-426-Fe(III) and PCN-426-Cr(III), respectively.

In summary, robust Fe(III) and Cr(III) MOFs with improved water stability and porosity can be synthesized using a PSMO strategy step by step. This strategy can overcome the challenges of incomplete exchange and low exchange rate, which are commonly encountered in the preparation of high-valence MOFs by metathesis. The following has been demonstrated in the context of the present invention: (1) A Mg-MOF is employed as a template so that the labile M-O bonds can drive the metal exchange to completion; and (2) the MOF template was first exchanged with low-oxidation-state but kinetically labile metal ions, which were subsequently oxidized to high oxidation state to accelerate the metal-exchange and at the same time preserve the integrity of the framework. The completely exchanged products PCN-426-Fe(III) and PCN-426-Cr(III) were obtained in a SC-SC transformation procedure and characterized by single crystal X-ray diffraction studies. In general, chromium MOFs were obtained in powder forms almost exclusively in the literature until PCN-426-Cr(III), which have been made through the PSMO synthetic route. Because MOFs based on high-valence metal ions are usually produced in amorphous or powder forms, PSMO is of critical importance for the synthesis and characterization of robust MOFs, which are otherwise difficult or unfeasible through traditional synthetic routes.

PSRMO

The PSRMO method described herein provided an ultra-stable mesoporous Cr-MOF; named PCN-333-Cr(III). It possesses a very large cage-like mesopore with a diameter of 5.5 nm. PCN-333-Cr(III) was obtained by heating freshly prepared PCN-333-Fe in a solution of $CrCl_2$ in dry N,N-dimethylformamide (DMF) at 85° C. under the protection of $N_2$. The color changes from brown reddish to deep green after about 30 minutes. After removing the unreacted Cr(II) salt, the green solid was exposed to the air to guarantee that the Cr(II) in the framework can be completely oxidized to +3 oxidation state which was verified by X-ray photoelectron spectroscopy (XPS). The completeness of metal metathesis of Fe by Cr was confirmed by inductive coupled plasma mass spectroscopy (ICP-MS) and energy-dispersive X-ray spectroscopy (EDS) results. Powder X-ray diffraction studies (PXRD) suggested that the metathesis product was isostructural with PCN-333-Fe. More importantly, the PCN-333-Cr possesses almost the same surface area and pore size distribution as its iron template (Table A, FIGS. 11a-11e).

Although several reports have demonstrated the feasibility of metal metathesis for thermodynamically inert MOFs, e.g. see Kim et al; J. Am Chem. Soc. 2012, 134, 18082, complete metal metathesis using them as templates has never been achieved mainly due to two reasons: (a) the dissociation of high valence metal ions from framework is thermodynamically unfavorable; (b) the dissociation rate of high valence ion is much slower than that of the divalent species due to the much higher activation energy. Therefore, long reaction time or elevated reaction temperature is required in order to achieve complete metathesis. However, under these scenarios, framework collapse is usually inevitable because high valence metal ions in the reaction media can generate acidic environments due to their large hydrolysis equilibrium constant.

The inventors have addressed these problems and solved them. Without wishing to be bound by theory, due to the labile coordination bonds between low valence metal ions and carboxylate ligands, MOFs constructed with divalent metal ions are good templates for complete metal metathesis. Therefore, complete metal metathesis would be feasible if the oxidation state of the high valence metal ions can be lowered by redox reaction during the exchange procedure. There are several prerequisite for the above process to take place: (1) the metal ions of the framework is oxidative and can be readily reduced under mild condition; (2) the reductant does not cause harsh conditions (for example, very low/high pH values) when it is oxidized; (3) the oxidation potential of the oxidant is much higher than the reduction potential of the reductant, resulting in irreversible redox reaction. PCN-333-Fe is composed of oxidative Fe(III) species while $CrCl_2$ matches the prerequisites to be a suitable reductant as well as an active entering metal species to metathesize with reduced Fe(II) in the intermediate framework. The M3+/M2+ electrode potentials for Fe and Cr are: 0.77V (Fe), −0.42V (Cr).30 The large potential difference indicates that redox reaction can irreversibly take place between Fe(III) and Cr(II) as indicated below:

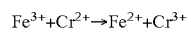

$$Fe^{3+}+Cr^{2+}\rightarrow Fe^{2+}+Cr^{3+}$$

Driven by concentration difference, the metal metathesis between Fe(II) in the framework and labile Cr(II) in the solution is thermo-dynamically and kinetically favorable.

What's more, it has been found that the use of anhydrous reaction solvent decelerated the hydrolysis of Cr(III) species. The absence of acidic condition contributes to the structural intactness of the as-metathesized MOF composed of fragile Cr(II)-O bond. This metal metathesis also benefits from several structural characteristics of PCN-333. First, the microcrystalline and mesoporous nature of PCN-333 allows for efficient diffusion of metal ions into the inner cavity of framework. On the other hand, the trimeric clusters in PCN-333 are able to accommodate both di- and trivalent metal ions by varying charges on the terminal ligands, the bridging oxygen atom, and/or the number of counterions. This assures the integrity of the metal clusters during redox/metathesis processes.

Several experimental results give solid evidences for the existence of redox involved route during the metathesis process. Instead of $CrCl_2$, metathesis of PCN-333-Fe(III) with $CrCl_3$ merely generates partially exchanged product even at higher temperature of 150° C. with elongated reaction time of 24 hours. The result illustrates that metal metathesis is retarded by the kinetic inertness of high valent metal ions. Moreover, PCN-333-Sc was synthesized as a template to metathesize with $CrCl_2$. Since Sc(III) can hardly be reduced to lower oxidation states by Cr(II) and the Sc(III)-O coordination bond is not as robust as Fe(III)-O bond, if the Cr(II) species is supposed to metathesize with Fe(III) ions of framework directly without undergoing redox reaction, complete metal exchange should also be observed for the metathesis of PCN-333-Sc with Cr(II). The mixture of PCN-333-Sc and CrCl$_2$ in dry DMF was heated at 85° C. for 30 minutes. The ICP-MS result shows that only one fifth of the scandium on the framework is exchanged with chromium. This observation implies that only if a thermodynamically more labile framework was generated during the experiment can a more robust framework, PCN-333-Fe, be completely metathesized, which means that the metathesis of PCN-333-Fe(III) with CrCl$_2$ undergoes the redox involved metathesis route with intermediate framework containing thermodynamically labile Fe(II)-O bond to facilitate the complete metathesis. Partially exchanged product is also generated in the metathesis of PCN-333-Al with CrCl$_2$ where Al(III) also cannot be reduced to lower oxidation states by Cr(II).

As expected, the chemical stability of PCN-333-Cr(III) is much enhanced compared with its iron derivative. Suspended in water, HCl aqueous solution (pH=0) and NaOH aqueous solution (pH=n) at room temperature for 24 hours, PCN-333-Cr(III) maintains the structural integrity without appreciable loss of crystallinity as confirmed by PXRD measurements. To demonstrate the intactness of porosity, N$_2$ isotherms were collected before and after each treatment. The results indicated that the void volume accessibility, the characteristic mesoporous adsorption pattern and the pore size distribution of PCN-333-Cr(III) after each treatment was unequivocally preserved (Table A, FIGS. 11a-11e). Remarkably the samples after each treatment even showed higher total adsorption amount than the as-prepared PCN-333-Cr(III). Without wishing to be bound by theory, this is probably because some insoluble Cr(III) compounds, generated during metal metathesis and trapped in the pores, were dissolved in aqueous solutions upon treatment. In contrast, PCN-333-Fe(III) is only stable in aqueous solutions at pH ranging from 3 to 9.

The above results have clearly demonstrated that employing kinetically inert metal ions is an efficient strategy for constructing ultrastable MOFs with high porosity. Since the association-dissociation equilibrium of metal-ligand coordination bond always exists, coordination bonds in a MOF also undergo association-dissociation process. In the aqueous solution, carboxylate ligand substitution around metal ions with other ligands from the solution, for example, water or hydroxyl group, may take place, which could lead to the breakdown of MOF structure. For two metal ions with the same valence, ligand substitution rate of the kinetically inert species is far slower than that of the labile one, which originates from the unique d electron configuration of the metal ion. The most common coordination mode of Cr(III) ion is six coordinated in the octahedral geometry with the three d electrons occupying in the t$_{2g}$ orbital. Ligand substitution of a high spin six-coordinated Cr(III) complex, CrL$_6$, by other ligand X takes place by dissociation of L from the complex

   (1)

followed by coordination of X

   (2)

The five-coordinated intermediate, CrL$_5$, always adopts square-planar geometry. Under this scenario, one of the three d electrons has to occupy the high energy b$_2$ orbital. The large energy difference between the five coordinated intermediate and its initial state leads to a high activation energy of ligand substitution for the Cr(III) ion which would dramatically slow down its ligand substitution rate. Meanwhile, the slow Cr-ligand dissociation rate also de-creases the hydrolysis rate of the carboxylate ligand which also contributes to the improvement of MOF stability.

Figure 31:
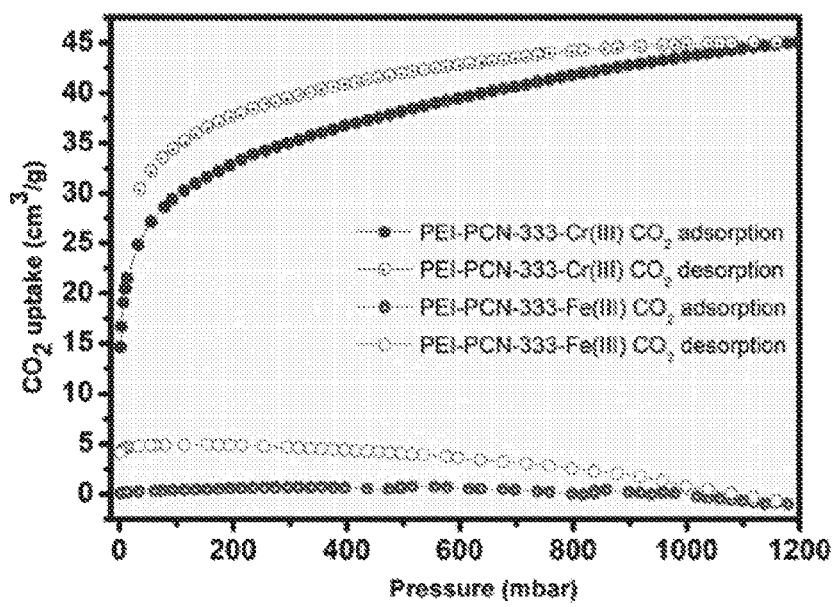
FIG. 31 shows CO2 adsorptions of PEI-incorporated PCN-333-Cr(III) and PEI-incorporated PCN-333-Fe(III).
Figure 32:
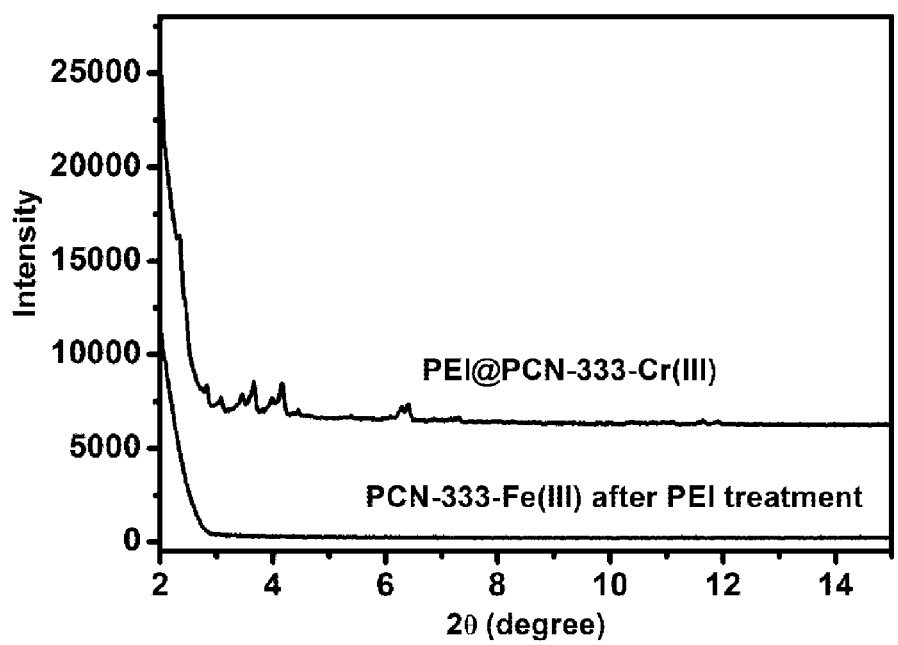
FIG. 32 shows PXRD patterns of PEI-incorporated PCN-333-Cr(III) and PEI-incorporated PCN-333-Fe(III).
Figure 33:
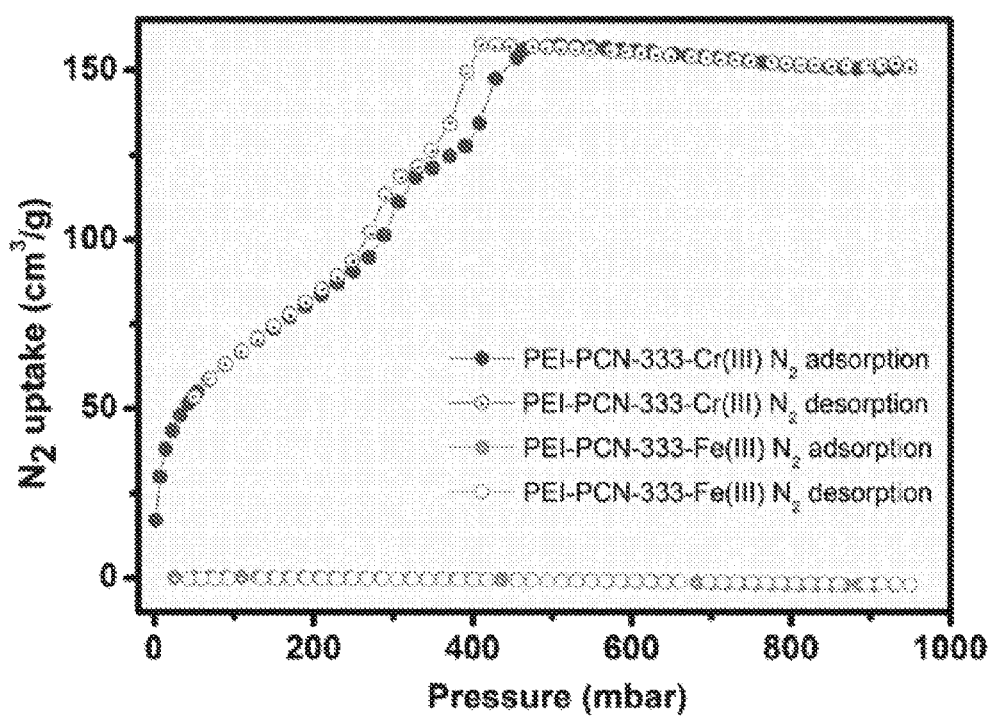
FIG. 33 shows N2 isotherms of PEI-incorporated PCN-333-Cr(III) and PEI-incorporated PCN-333-Fe(III)

By taking advantage of the superior chemical stability of PCN-333-Cr(III), alkylamine was incorporated in PCN-333-Cr(III) aiming to improve the CO$_2$ adsorption capacity. Branched polyethylenimine (PEI, Mw=800) is selected due to the high density of amine groups on each molecule. After PEI treatment the solid maintained its crystallinity with CO$_2$ adsorption capacity of 8.4 wt % at 1 bar (FIG. 31). In contrast, PCN-333-Fe(III) fully lost its crystallinity and porosity after PEI treatment according to PXRD pattern and N$_2$ isotherm measurement (FIGS. 32 and 33).

TABLE A

BET Surface Areas & DFT Pore Sizes Summary

| | BET surface area/ m2 g−1 | Total Volume in Pores/ cm3 g−1 | Total Area in Pores/ m2 g−1 |
|---|---|---|---|
| PCN-333-Fe(III) | 2427 | 2.72 | 1603 |
| PCN-333-Cr(III) | 2548 | 2.30 | 1611 |
| PCN-333-Cr(III) treated with water | 2742 | 2.69 | 1759 |
| PCN-333-Cr(III) treated with pH = 0 solution | 2678 | 2.66 | 1717 |
| PCN-333-Cr(III) treated with pH = 11 solution | 2610 | 2.54 | 1656 |

In conclusion, we report a reductive labilization-metal metathesis route for the construction of ultrastable Cr(III) based mesoporous MOFs from a robust iron based template. The whole process includes (1) reduction of Fe(III) on the framework backbone to Fe(II) by Cr(II); (2) metal metathesis between Fe(II) and Cr(II); (3) oxidation of Cr(II) in the framework to Cr(III). The existence of Fe(II) intermediate is proved by incomplete metathesis of PCN-333-Sc with CrCl$_2$, as well as PCN-333-Al with CrCl$_2$. After metathesis, PCN-333-Cr has demonstrated enhanced chemical stability in aqueous solutions at pH 0 to 11 whereas PCN-333-Fe can only survive in solution at pH 3 to 9. Significantly, PCN-333-Cr is robust enough to bear the harsh condition of alkylamine solution, display high CO$_2$ adsorption capacity after PEI incorporation. Overall, the method represents a new platform to synthesize ultrastable MOFs with high porosity for practical applications.

EXAMPLES

Materials and Instrumentation

Magnesium Nitrate Hexahydrate (Mg(NO$_3$)$_2$.6H$_2$O), Chromium(II) chloride (CrCl$_2$), Iron(II) Chloride (FeCl$_2$), N, N-dimethylformamide (DMF), Ethyl alcohol (EtOH), acetone, toluene, 2,4,6-trichloro-1,3,5-triazine, anhydrous aluminium chloride (AlCl$_3$), scandium(III) chloride hexahydrate (ScCl$_3$.6H$_2$O), chloroform (CHCl$_3$), 1,3,5-benzentricarboxylic acid (BTC), 2,5-dihydroxyterephthalic acid (DOBDC), TiO$_2$ were purchased from Alfa Aesar. All commercial chemicals were used without further purification unless otherwise mentioned. Powder X-ray diffraction (PXRD) was carried out with a BRUKER D8-Focus Bragg-Brentano X-ray Powder Diffractometer equipped with a Cu sealed tube (λ=1.54178) at 40 kV and 40 mA. Thermogravimetric analyses (TGA) were carried out on a Shimadzu TGA-50 thermal analyzer from room temperature to 600° C. at a ramp rate of 2° C./min in a flowing nitrogen atmosphere. Nuclear magnetic resonance (NMR) data were collected on a Mercury 300 spectrometer. Gas sorption measurements were conducted using a Micrometritics ASAP 2020 system at different temperatures. Energy dispersive X-ray spectroscopy was carried out by JEOL JSM-7500F with Oxford EDS system equipped with X-ray mapping. X-ray photoelectron spectroscopy was carried out by Kratos Axis Ultra Imaging X-ray photoelectron spectrometer.

Ligand Synthesis (TMQPTC)

Synthesis of F: A solution of NaNO$_2$ (2.32 g) in 20 mL water was added to a cloudy mixture of E (6.6 g, 27.8 mmol) in 30 mL 2M hydrochloric acid at 0° C. After stirred at 0° C. for 45 minutes, an ice-cold KI aqueous solution was added. Then mixture changed to dark red and sticky. After 100 mL CH$_2$Cl$_2$ was added, the mixture was allowed to stir at RT for 4 hours. The aqueous phase was washed with

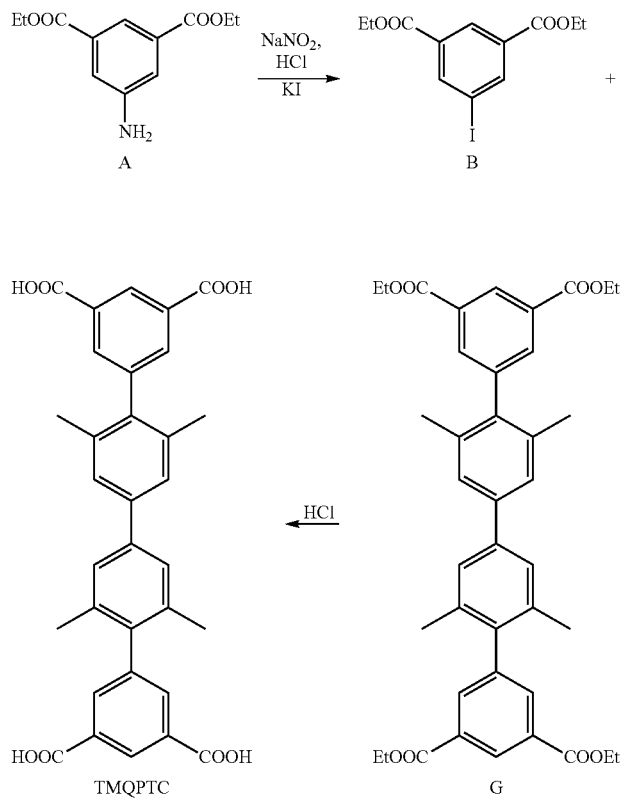
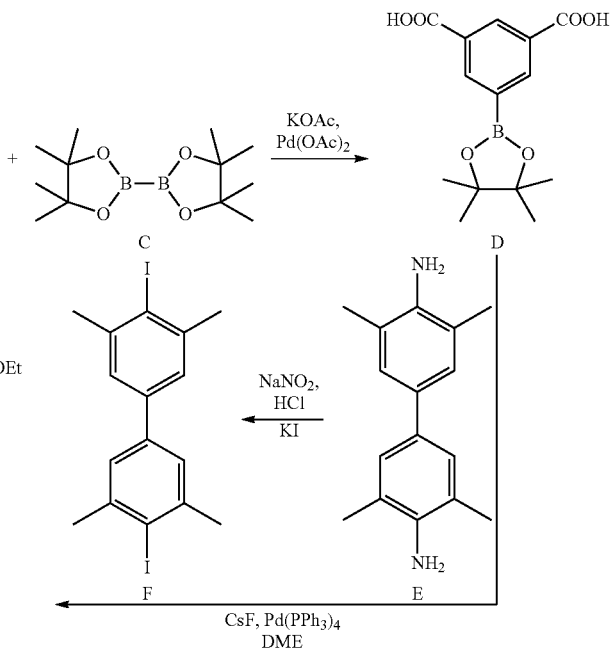

Synthesis of B: A solution of NaNO$_2$ (2.32 g) in 20 mL water was added to a cloudy mixture of A (6.6 g, 27.8 mmol) in 30 mL 2M hydrochloric acid at 0° C. After stirred at 0° C. for 45 minutes, an ice-cold KI aqueous solution was added. Then mixture changed to dark red and sticky. After 100 mL CH$_2$Cl$_2$ was added, the mixture was allowed to stir at RT for 4 hours. The aqueous phase was washed with CH$_2$Cl$_2$ three times. The combined organic phases were dried with MgSO$_4$. After the solvent was removed, the crude product was purified by column chromatography with Ethyl Acetate: Hexans=4:1 as the elute (8.8 g, Yield. 91%). $^1$H NMR (Acetone): δ=1.4 (t, 3H), 4.4 (q, 2H), 8.2 (s, 2H), 8.6 (s, 1H).

Synthesis of D: Degassed dry DMF (18 mL) was added to a mixture of B (3.48 g, 10 mmol), C (3.1 g, 12 mmol), potassium acetate (2.2 g, 24 mmol), and Pd(OAc)$_2$ (49 mg, 0.22 mmol). The mixture was heated to 90° C. (oil bath) for 24 h. After cooling to room temperature, the solution was added dropwise to water (90 mL) and stirred vigorously for 10 min. The solid was collected by filtration and purified through column chromatography on silica gel (hexane/ethyl acetate, 80:20, second point) to afford product as a white solid (2.01 g, 86%). $^1$H NMR (CDCl$_3$): δ=1.346 (s, 12H), 1.396 (t, 6H), 4.392 (q, 4H), 8.600 (d, 2H), 8.739 (t, 1H).

CH$_2$Cl$_2$ three times. The combined organic phases were dried with MgSO$_4$. After the solvent was removed, the crude product was purified by column chromatography with Ethyl acetate: Hexans=4:1 as the eluent. $^1$H NMR (CDCl$_3$): δ=2.538 (s, 12H), 7.261 (s, 4H).

Figure 6:
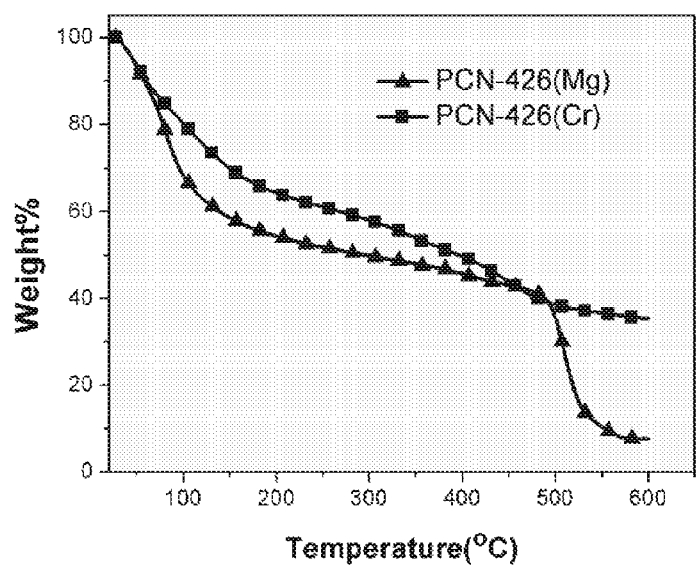
FIG. 6 shows the thermogravimetric (TG) analyses for as-synthesized PCN-426-Cr(III) and PCN-426-Mg.

Synthesis of TMQPTC: A 250-mL Schlenk flask was charged with of D (0.8 g, 3.05 mmol), F (3.7 g 8 mmol), CsF (4 g, 26.4 mmol), and 0.2 g of Pd(P(Ph)$_3$)$_4$. 120 ml of DME was degassed and transferred. A water condenser was then equipped and the flask was heated to reflux under the nitrogen for 72 hours. The solvent was dried on rotary evaporator. The residue was dissolved by CH$_2$Cl$_2$ and purified by column chromatography to white crystal. The white crystal was dissolved in a 500-mL Schlenk flask with 200 mL mixture of THF and MeOH (v/v=1:1). 100 mL of 0.3M NaOH aqueous solution was added. The flask was heated to reflux overnight. The solution is then acidified by diluted hydrochloric acid to give white precipitate, which was filtered and washed with water several times to get TMQPTC 1.2 g (Yield. 68%). $^1$H NMR (DMSO): δ=2.051 (s, 12H), 7.516 (s, 4H), 7.925 (d, 4H), 8.490 (t, 2H). The $^1$H NMR spectrum of TMQPTC is shown in FIG. 6.

Synthesis of Ligand (H₃TATB)

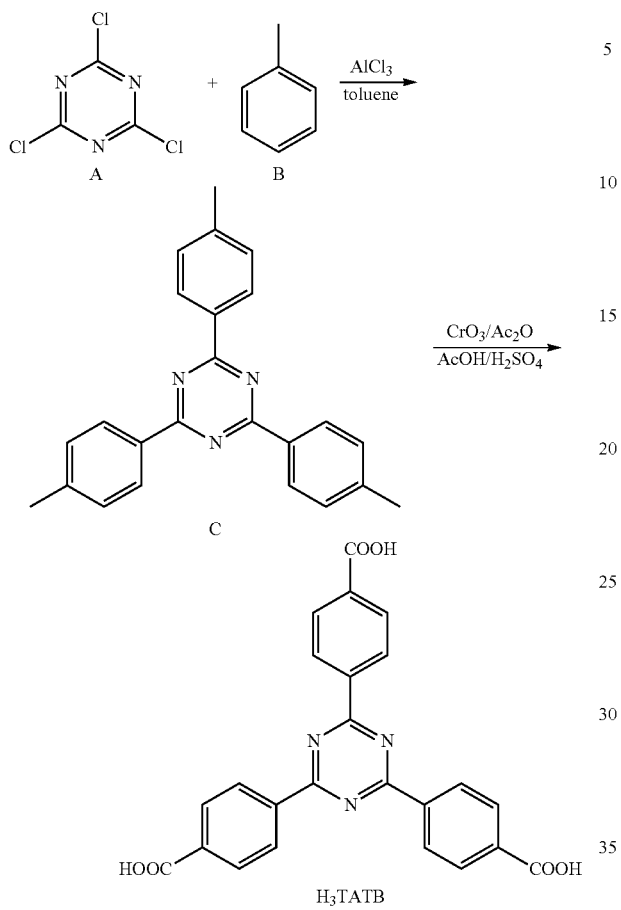

Synthesis of C: AlCl₃ (20 g) was added to a 250 ml three-connected flask containing dry toluene (50 mL). The temperature was increased to 60° C. C₃N₃Cl₃ (8.3 g) was added in portions with about 0.2 g each time for about 1 hour. After the C₃N₃Cl₃ was added, the mixture was allowed to disturb for one more hour (or overnight). The resultant red sticky oil was poured into a large amount of ice water to kill the catalyst. CHCl₃ (100 mL) is added. The water layer is decanted, and the organic layer was filtered. Methanol is added into CHCl₃ to precipitate some needle-like solid. The rest solid is recrystallized with hot toluene to afford white needle-like crystalline solids (dissolve solid in hot toluene, then place in refrigerator). $^1$H NMR (300 MHz, CDCl₃): δ=2.46 (s, 9H), 7.35 (d, 6H), 8.64 (d, 6H) ppm.

Synthesis of H₃TATB: A 500 mL three-necked flask was charged with C (2.78 g) dissolved in acetic acid (70 mL). Then add of H₂SO₄ (4.4 mL). Chromium oxide (7.2 g) was dissolved in acetic anhydride (4.8 mL) with stirring, then carefully added into the solution slowly, using a cold water-ice bath to keeping the temperature below 50° C. The resulting black-brown slurry was stirred overnight. The reaction mixture was poured into 300 mL cold water, stirred (1 hour) to mix, then filtered. The solid was washed with water to remove the chromium acid. The resultant white solid was dissolved in 200 mL 2N NaOH solution. After the unreacted starting material was removed by filtration, the solution was acidified with 10% HCl solution to give white crude product precipitate (until pH<3). The crude product was filtered and dried. Recrystallization from DMF gave pure product as a white solid. $^1$H NMR (300 MHz, DMSO): δ=8.20 (d, 6H), 8.85 (d, 6H), 13.35 (s, 3H) ppm.

Synthesis of Ligand (H₃BTB)

In the following H₃BTB is referred to as L15.

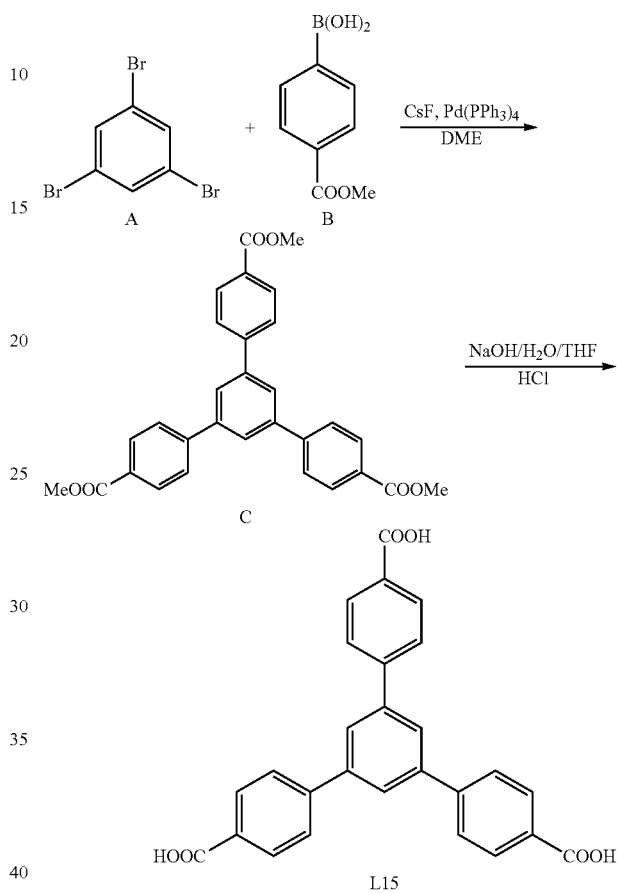

Synthesis of C: A (2 g, 6.4 mmol), B (3.78 g, 21 mmol), CsF (3 g, 20 mmol) and Pd(PPh₃)₄(0.2 g, 0.17 mmol) was added to a 250 mL flask, and the flask was connected to Schlenk line. 200 mL DME was degassed and added through a canula. The mixture was refluxed under the nitrogen for 48 hours. The solution was dried on rotary evaporator. 100 mL H₂O was added and then extract with CHCl₃. The residue was subjected to column chromatography on silica gel (Ethyl acetate:Hexane=20:80) to yield the title compound C as white solid 2.0 g. (Yield: 65%).

Synthesis of L15: Compound C (2.0 g, 4.2 mmol) was suspended in 60 mL THF/MeOH (v:v=1:1), and 30 mL 10% NaOH solution was added. The mixture was stirred overnight. The pH value was adjusted to approximately 2 using hydrochloric acid. The resulting white precipitate was collected by filtration, washed with water, and dried under vacuum to give L15 (1.7 g, 92%). $^1$H NMR (CDCl₃): δ=3.97 (s, 9H), 7.90 (d, 2H), 8.06 (d, 2H), 8.44 (d, 2H) 8.49 (t, 1H).

Syntheses of PCN-426 Fe(III)—Example 1

Synthesis of PCN-426-Mg: Mg(NO₃)₂.6H₂O (100 mg), TMQPTC (30 mg), a solution of DMF, EtOH and H₂O (v:v:v=4:1:1) 15 mL were charged in a Pyrex vial. The mixture was heated in 100° C. oven for 24 h. After cooling down to room temperature, colorless cubic crystal was harvested (21 mg, Yield: 48%).

Figure 3:
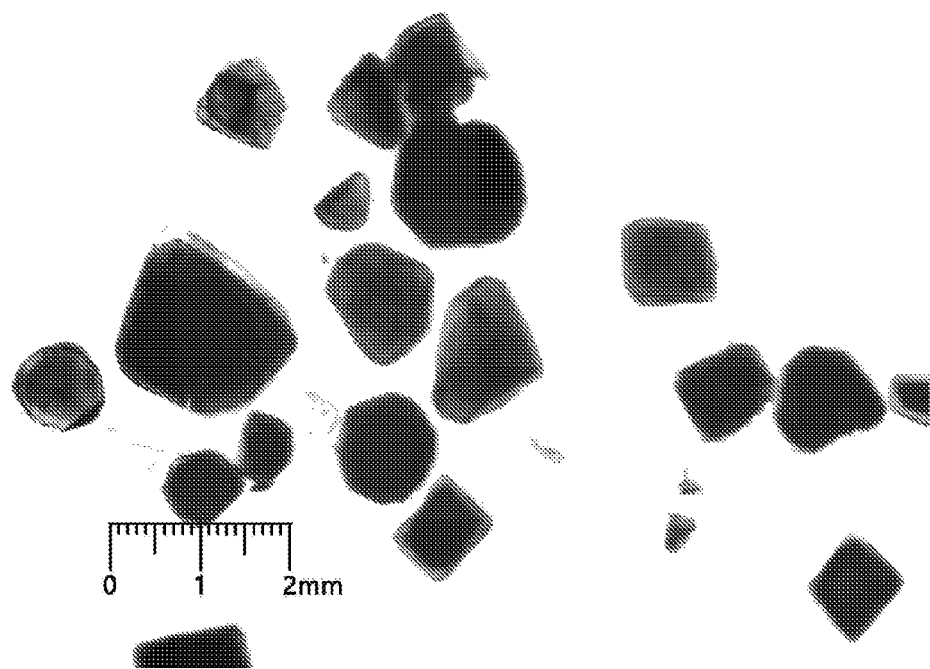
FIG. 3 shows an optical microscope image of PCN-426-Fe(III).

Synthesis of PCN-426-Fe(III): As-synthesized PCN-426-Mg 25 mg was washed with dry DMF for several times. The mixture was bubbled with nitrogen for 15 min, and then 40 mg anhydrous $FeCl_2$ was added under the protection of nitrogen. The color obviously changed from colourless to purple in 20 min. In order to make exchange completely, the reaction was allowed to continue for 3 hours. Then the sample was bubbled with oxygen for 15 min before the $FeCl_2$ solution was removed by syringe. The solid was washed with fresh DMF to get PCN-426-Fe(III). An optical microscope image of PCN-426 (Fe) crystals is shown in FIG. 3.

Synthesis of PCN-426 (Cr)—Example 2

Figure 4:
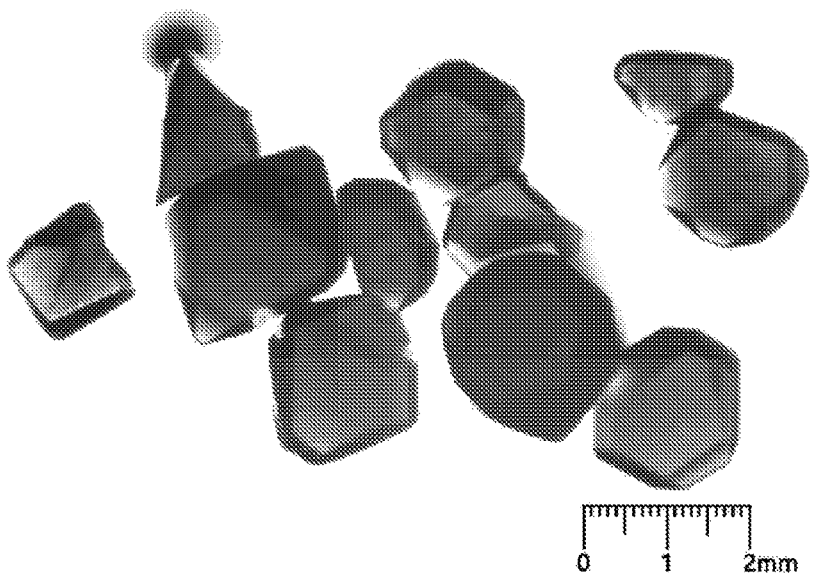
FIG. 4 shows an optical microscope image of PCN-426-Cr(III).

PCN-426-Cr-precursor and PCN-426-Cr(III) were synthesized using the same procedure described above in relation to the synthesis of PCN-426-Fe(III) except using $CrCl_2$ instead of $FeCl_2$. An optical microscope image of PCN-426 (Cr) crystals is shown in FIG. 4.

Results for PCN-426-Cr(III), PCN-426-Fe(III)

X-Ray Crystallography

Single crystal X-ray data of PCN-426-Mg, PCN-426-Fe(III) and PCN-426-Cr(III) were collected on a Bruker Smart Apex diffractometer equipped with a low temperature device (110K) and a fine-focus sealed-tube X-ray source (Mo-Kα radiation, λ=0.71073 Å, graphite monochromated). The data frames were collected using the program APEX2 and processed using the program SAINT routine within APEX2. The data were corrected for absorption and beam corrections based on the multi-scan technique as implemented in SADABS. The structures were solved by direct method and refined by full-matrix least-squares on $F^2$ with anisotropic displacement using the SHELXTL software package. Non-hydrogen atoms were refined with anisotropic displacement parameters during the final cycles. Hydrogen atoms on carbon and oxygen were calculated in ideal positions with isotropic displacement parameters set to 1.2×Ueq of the attached atoms. In the structure, free solvent molecules were highly disordered, and attempts to locate and refine the solvent peaks were unsuccessful. Contributions to scattering due to these solvent molecules were removed using the SQUEEZE routine of PLATON; the structures were then refined again using the data generated. The contents of the solvent region are not represented in the unit cell contents in the crystal data. Crystallographic data and structural refinements are summarized in Table 1:

TABLE 1

Crystal data and structural refinements for PCN-426 Mg(II), PCN-426-Fe(III) and PCN-426-Cr(III).

|  | PCN-426-Mg | PCN-426-Fe(III) | PCN-426-Cr(III) |
|---|---|---|---|
| CCDC | 978944 | 978943 | 978945 |
| Formula | $Mg_3C_{32}H_{22}O_{12}$ | $Fe_3C_{32}H_{25}O_{12}$ | $Cr_3C_{32}H_{25}O_{12}$ |
| Formula weight | 671.43 | 769.07 | 757.52 |
| Crystal Color/Shape | Colorless Block | Brown Block | Blue Block |
| Crystal System | Cubic | Cubic | Cubic |
| Space Group | Fm$\bar{3}$m | Fm$\bar{3}$m | Fm$\bar{3}$m |
| a (Å) | 41.091(4) | 40.77(4) | 40.881(8) |
| V (Å$^3$) | 69381(12) | 67753(126) | 68323(23) |
| Z | 24 | 24 | 24 |
| $d_{calcd.}$ (g/cm$^3$) | 0.386 | 0.452 | 0.442 |
| μ(mm$^{-1}$) | 0.044 | 0.398 | 0.299 |
| F(000) | 8304 | 9384 | 9240 |
| $\theta_{max}$ [deg] | 23.99 | 23.54 | 24.50 |
| Completeness | 99.5% | 99.8% | 99.8% |
| Collected reflections | 157171 | 71593 | 80832 |
| Unique reflections | 2693 | 2513 | 2811 |
| Parameters | 74 | 56 | 56 |
| Restraints | 17 | 25 | 25 |
| $R_{int}$ | 0.1291 | 0.1498 | 0.1737 |
| R1 [I > 2σ(I)] | 0.1993 | 0.1289 | 0.1795 |
| wR2 [I > 2σ(I)] | 0.2995 | 0.2529 | 0.3935 |
| R1 (all data) | 0.2548 | 0.2673 | 0.3268 |
| wR2 (all data) | 0.3320 | 0.3099 | 0.4368 |
| GOF on $F^2$ | 1.009 | 1.007 | 1.914 |
| $\Delta\rho_{max}/\Delta\rho_{min}$ [e · Å$^{-3}$] | 0.457/−0.387 | 0.496/−0.512 | 0.576/−0.370 |

$R1 = \Sigma||F_o| - |F_c||/\Sigma|F_o|$; $wR2 = \{\Sigma[w(F_o^2 - F_c^2)^2]/\Sigma[w(F_o^2)^2]\}^{1/2}$; $w^{-1} = \sigma^2(F_o)^2 + (aP)^2 + bP$.

TABLE 2

EDS for PCN-426-Fe(III)

| Element | Weight % | Atomic % |
|---|---|---|
| C K | 51.73 | 68.05 |
| O K | 25.75 | 25.43 |
| Mg K | 0.00 | 0.00 |
| Cl K | 0.88 | 0.39 |
| Fe L | 21.64 | 6.12 |
| Totals | 100.00 |  |

Refinement Details:

Diffraction frames of all three crystals were integrated in Cubic F by APEX2. XPREP suggested that Fm$\bar{3}$m should be the best choice with lowest CFOM factor, in which it is transformed to get Fourier peaks by direct method. Since the ligand geometry is poor, distance restraints on phenyl rings and C—C bonds were applied in the structural refinements. As for the metal clusters, it shows unreasonable coordination mode and enormous atomic displacement parameters (ADPs) on the metal atoms and their attached side oxygen atoms. We regarded the four metal atoms on the square part as two sets of disorders, which rationally represent three metal atoms in one cluster. For PCN-426-Mg compound, there are four carboxylate groups, one $\mu_3$-oxygen and three Mg(II) forming one cluster; therefore, the attached side oxygen should be identified as non-charged solvents. For PCN-426-Fe(III) and Cr(III) compounds, however, the attached side oxygen should be assigned as OH$^-$ to make charge balance.

In order to kill alerts about abnormal ADPs, proper EADP command was employed on problematic phenyl rings to fix most of these warnings. Other alert about $\mu_3$-oxygen with low Ueq was triggered by the enormous Ueq of its neighbor atoms, Cr$_2$. We attribute this large Ueq to the metal positions involving 50% disorder and post-synthetic procedure of metal exchange. Remarkably, the R values of the structure refinement are 19.93%, 17.95%, 12.89% for PCN-426-Mg, Cr(III), Fe(III), inferring that the Fe-based compound shows better crystalline quality than original Mg-based one does. The squeezed void volumes were 52026 Å$^3$ (Mg), 51074 Å$^3$ (Cr), 51769 Å$^3$ (Fe), equivalent to 74.98%, 74.75%, 76.41% of the corresponding unit cell.

X-Ray Photoelectron Spectroscopy (XPS) Analysis

In order to confirm the oxidation state of products, we preformed XPS measurement for PCN-426-Fe(III), PCN- 426-Cr(III) as well as their corresponding precursors (named as PCN-426-Fe-precursor and PCN-426-Cr-precursor, synthesis detail above). FIG. 1 represents the Fe 2p region for PCN-426-Fe(III) and PCN-426-Fe-precursor. For the spectrum of PCN-426-Fe(III), the Fe$2p_{3/2}$ signal at 711.6 eV and Fe$2p_{1/2}$ signal at 725.3 eV well indicate the $Fe^{3+}$ species in sample. Meanwhile, the Fe $2p_{3/2}$ satellite structures are found between 720 and 716 eV. For the spectrum of PCN-426-Fe-precursor, the absence of satellite is caused by the overlapping of both satellites for $Fe^{2+}$ and $Fe^{3+}$ and indicates the coexistence of $Fe^{2+}$ and $Fe^{3+}$. The partially oxidation from $Fe^{2+}$ to $Fe^{3+}$ is caused by the unavoidably exposed in atmosphere when transferring sample from reaction container to the chamber of XPS instrument. In the same way, the $Cr^{2+}$ was oxidized to $Cr^{3+}$ without clear $Cr^{2+}$ peak being detected in PCN-426-Cr-precursor because of much higher activity of $Cr^{2+}$. However, the $Cr^{3+}$ species can be confirmed by the Cr $2p_{3/2}$ peak at 577 eV and Cr $2p_{1/2}$ peak at 587 eV for PCN-426-Cr(III) which conclude the success of metal exchange and sequent oxidation of metal nodes.

Gas Adsorption Measurement

The adsorption characteristics of PCN-246-Cr(III), PCN-426-Fe(III), and PCN-426-Mg were measured.

Before measurements were carried out, as-synthesized samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2Cl_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

FIG. 5 shows the $N_2$ uptake (adsorption) measured for PCN-246-Cr(III), PCN-426-Fe(III), and PCN-426-Mg.

Thermogravimetric Analysis

About 15 mg samples were was heated on a TGA-50 (Shimadzu) thermogravimetric analyzer from room temperature to 600° C. at a rate of 2° C. $min^{-1}$ under $N_2$ flow of 15 mL $min^{-1}$.

FIG. 6 shows the thermogravimetric analysis trace for a fresh sample of PCN-426-Cr(III) compared to PCN-426-Mg.

Figure 7:
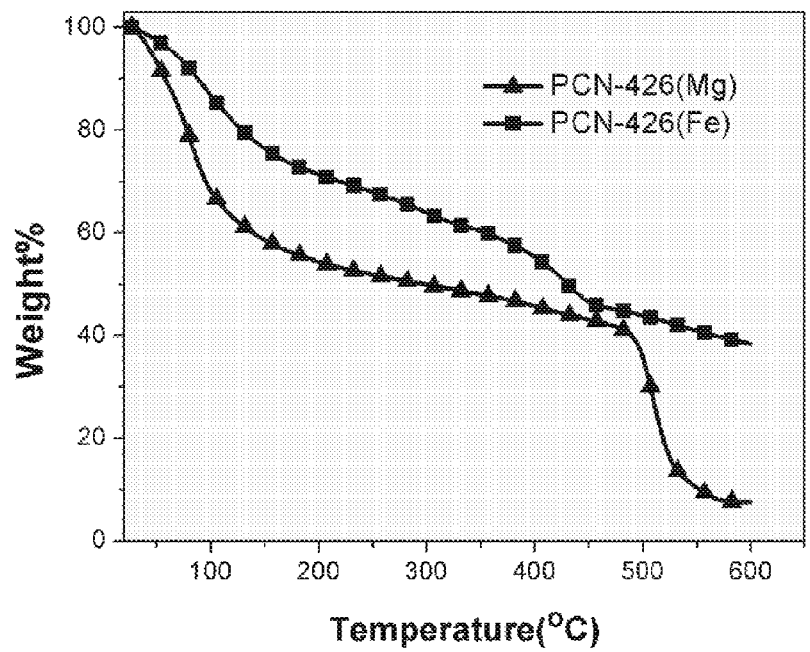
FIG. 7 shows the thermogravimetric (TG) analyses for as-synthesized PCN-426-Fe(III) and PCN-426-Mg.

FIG. 7 shows the thermogravimetric analysis trace for a fresh sample of PCN-426-Fe(III) compared to PCN-426-Mg.

Powder X-Ray Diffraction Pattern

Figure 8:
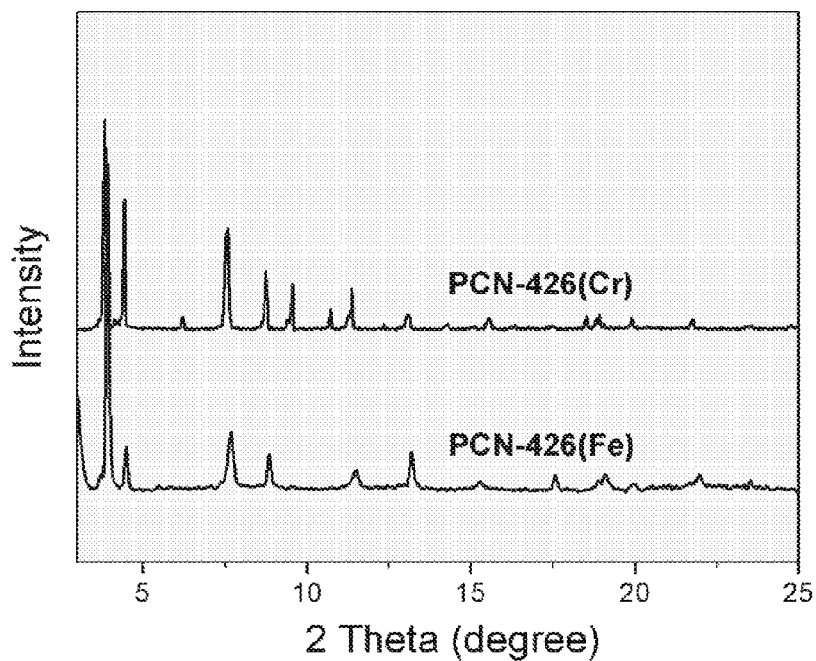
FIG. 8 shows PXRD patterns of PCN426-Fe(III) and PCN-426-Cr(III).

The powder x-ray diffraction pattern (PXRD) for PCN-426-Cr(III) and PCN-426-Fe(III) are shown in FIG. 8.

PCN-260-Cr(III)

Synthesis of PCN-260-Cr(III)

Figure 9:
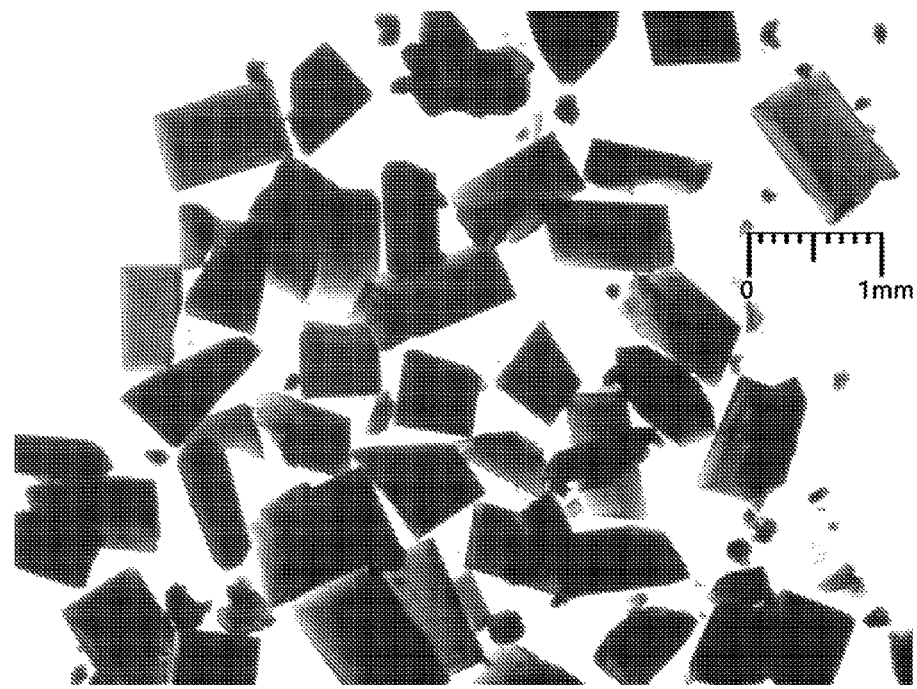
FIG. 9 shows an optical microscope image of PCN-260-Fe(III).

Synthesis of PCN-260-Fe: H$_3$BTB (15 mg), Fe$_2$CoO(CH$_3$COO)$_6$ (5 mg) and acetic acid (0.25 ml) in 2 mL of NMP were ultrasonically dissolved in a Pyrex vial. The mixture was heated in 150° C. oven for 24 h. After cooling down to room temperature, dark brown crystals of PCN-260(Fe) were harvested by filtration (Yield. 80%). Crystal size: 0.5 mm-2 mm. An optical microscope image of the crystals of PCN-260-Fe are shown in FIG. 9.

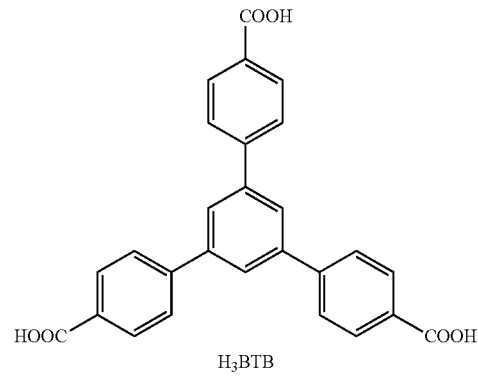

H$_3$BTB

Figure 10:
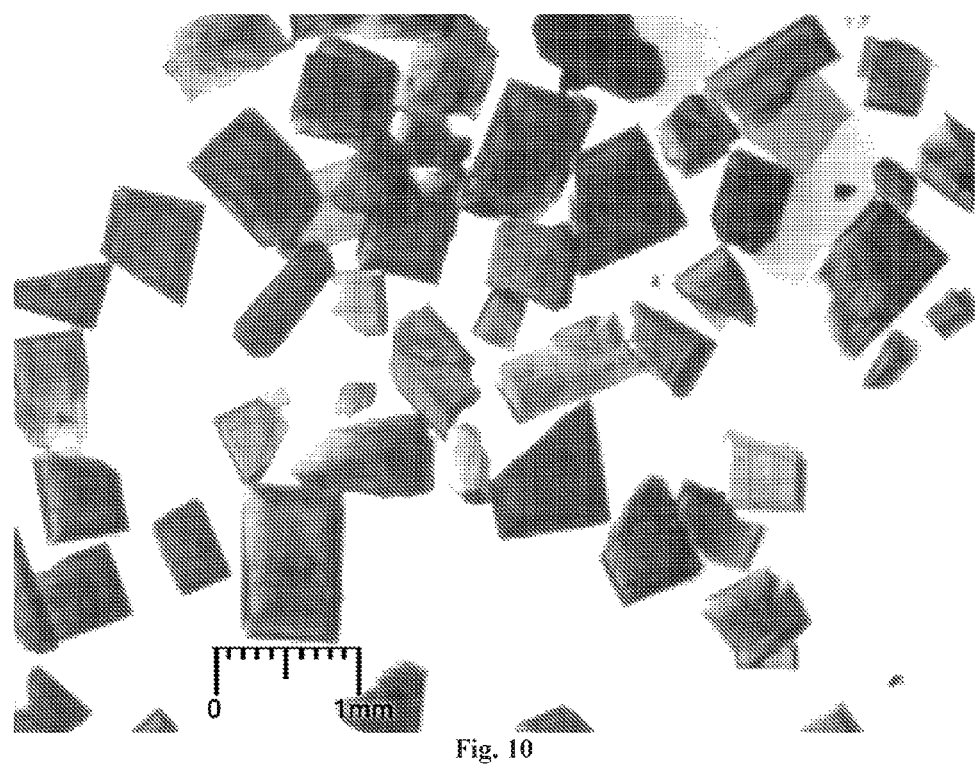
FIG. 10 shows an optical microscope image of PCN-260-Cr(III).
Figure 11A:
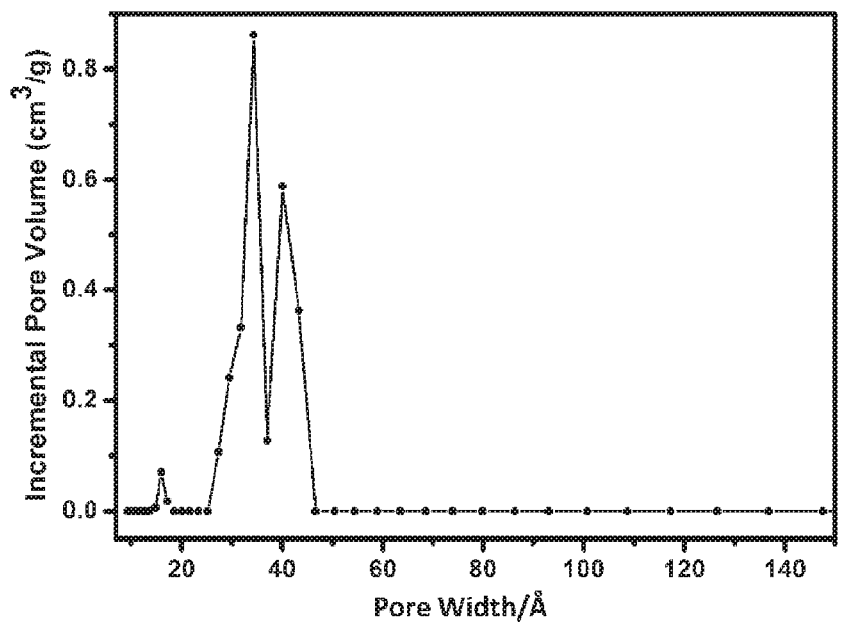
FIG. 11*a* shows the pore size distribution of PCN-333-Fe(III).
Figure 11B:
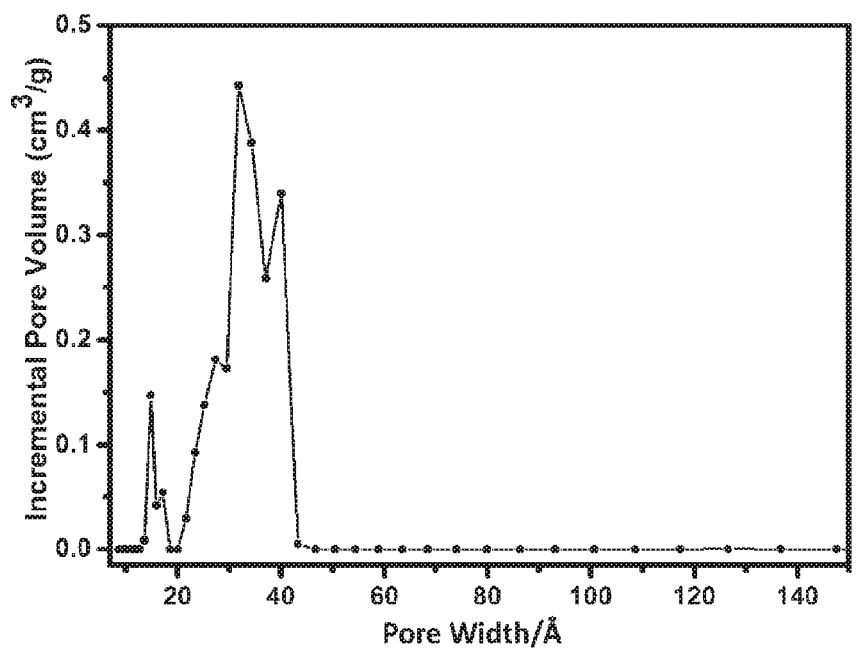
FIG. 11*b* shows the pore size distribution of PCN-333-Cr(III).
Figure 11C:
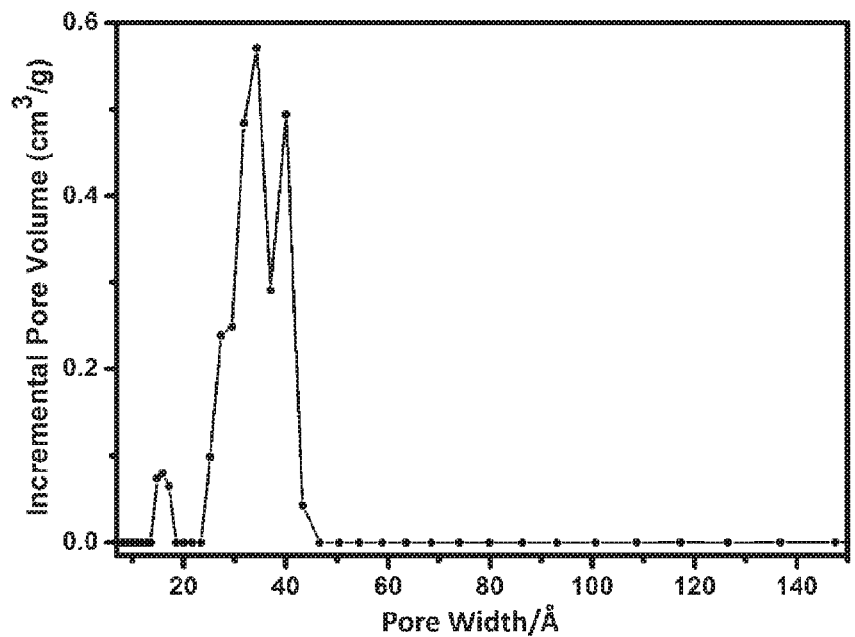
FIG. 11*c* shows the pore size distribution of PCN-333-Cr(III) after water treatment.
Figure 11D:
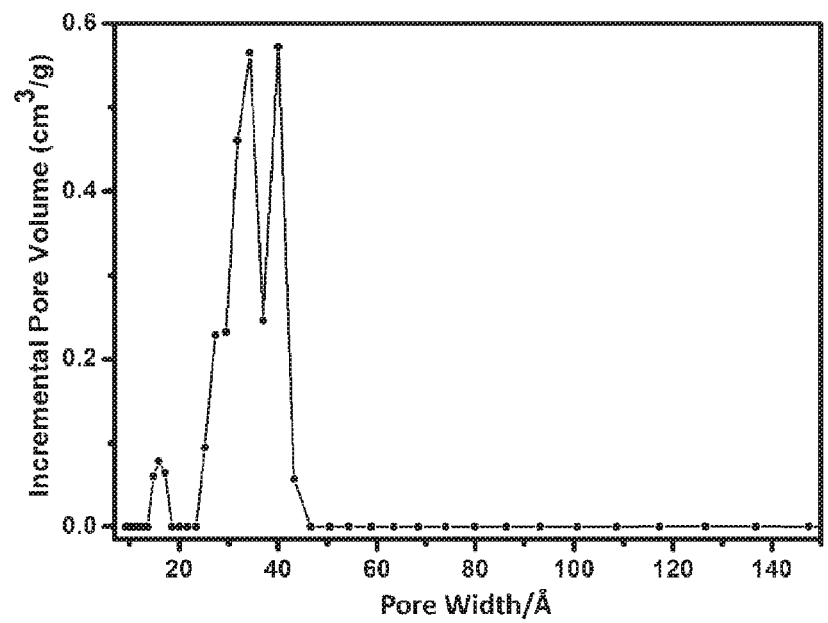
FIG. 11*d* shows the pore size distribution of PCN-333-Cr(III) treated with pH=0 solution.
Figure 11E:
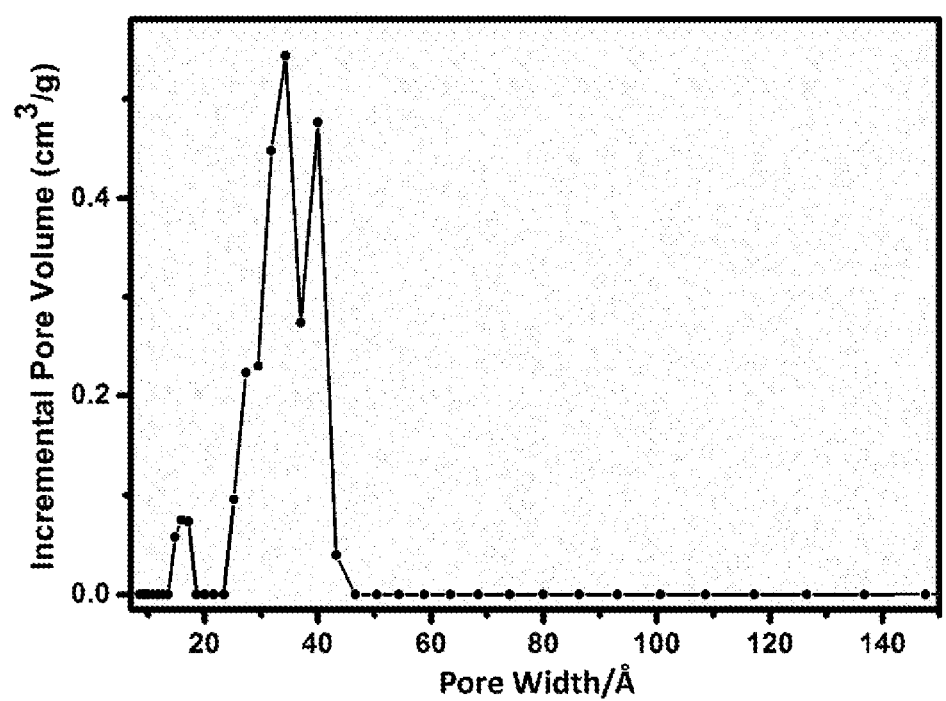
FIG. 11*e* shows the pore size distribution of PCN-333-Cr(III) treated with pH=11 solution.

Synthesis of PCN-260-Cr(III): 10 mg single crystals of PCN-260-Fe and 30 mg CrCl$_2$ were combined in 2 mL DMF under nitrogen. The mixture is then heated at 120° C. for 6 hours before cooling down to the room temperature. The solvent was discarded and the single crystals were washed with DMF for several times until the solution was colorless. Crystal size: 0.5 mm-2 mm. An optical microscope image of PCN-260-Cr(III) is shown in FIG. 10.

Crystallographic data and structural refinements for PCN-260-Fe and PCN-260-Cr(III) are summarized in Table 2a below:

TABLE 2a

Crystal data and structural refinements for PCN-260 (Fe) and PCN-260-Cr(III).

| | PCN-260-Fe(III) | PCN-260-Cr(III) |
|---|---|---|
| CCDC | 975820 | XXXXXX |
| Formula | Fe2 Co C54 H30 O16 | Cr3 C54 H34 O16 |
| Formula weight | 1105.41 | 1089.34 |
| Crystal Color/Shape | Orange Rectangle | Dark Green Rectangle |
| Crystal System | Orthorhombic | Orthorhombic |
| Space Group | Pca21 | Pca21 |
| a (Å) | 36.155(4) | 34.512(1) |
| b (Å) | 18.566(2) | 18.433(3) |
| c (Å) | 48.725(6) | 46.518(9) |
| α (°) | 90 | 90 |
| β (°) | 90 | 90 |
| γ (°) | 90 | 90 |
| V (Å$^3$) | 32707(6) | 29594.02 |
| Z | 8 | 8 |
| $d_{calcd.}$ (g/cm$^3$) | 0.449 | 0.489 |
| μ(mm$^{-1}$) | 0.297 | 0.241 |
| F(000) | 4488 | 4444 |
| $θ_{max}$ [deg] | 24.78 | 26.7 |
| Completeness | 99.8% | 98% |
| Collected reflections | 303240 | 306549 |
| Unique reflections | 56026 | 61053 |
| Parameters | 830 | 1204 |
| Restraints | 1 | 1 |
| $R_{int}$ | 0.0733 | 0.1422 |
| R1 [I > 2σ(I)] | 0.0630 | 0.1317 |
| wR2 [I > 2σ(I)] | 0.1264 | 0.3129 |
| R1 (all data) | 0.0914 | 0.1689 |
| wR2 (all data) | 0.1339 | 0.3537 |
| GOF on F$^2$ | 1.000 | 1.300 |
| $Δρ_{max}/Δρ_{min}$ [e · Å$^{-3}$] | 0.793/−0.688 | 1.227/−0.653 |

R1 = Σ||F$_o$| − |F$_c$||/Σ|F$_o$|; wR2 = {Σ[w(F$_o^2$ − F$_c^2$)$^2$]/Σ[w(F$_o^2$)$^2$]}$^{1/2}$; w$^{-1}$ = σ$^2$(F$_o$)$^2$ + (aP)$^2$ + bP.

Gas Adsorption Measurement

The adsorption characteristics of PCN-260-Cr(III) were measured.

Before measurements were carried out, as-synthesized samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2C_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

Thermogravimetric Analysis

About 15 mg samples were was heated on a TGA-50 (Shimadzu) thermogravimetric analyzer from room temperature to 600° C. at a rate of 2° C. $min^{-1}$ under $N_2$ flow of 15 mL $min^{-1}$.

Figure 12:
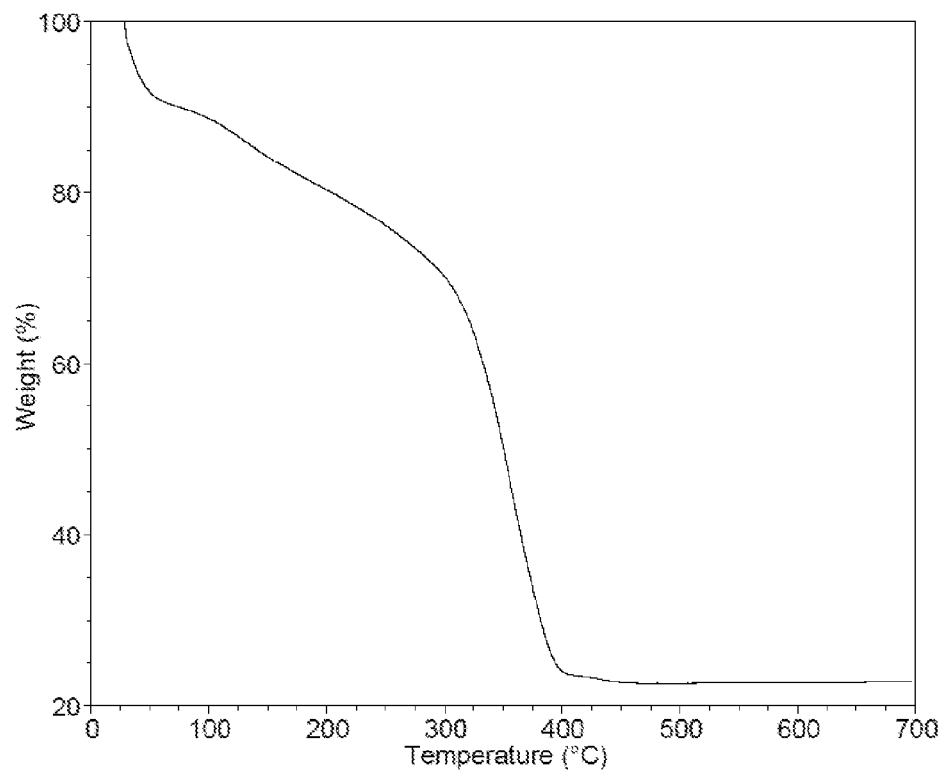
FIG. 12 shows the thermograyimetric (TG) analyses for as-synthesized PCN-260-Cr(III).

FIG. 12 shows the thermogravimetric analysis trace for a fresh sample of PCN-260-Cr(III).

Powder X-Ray Diffraction Pattern

Figure 13:
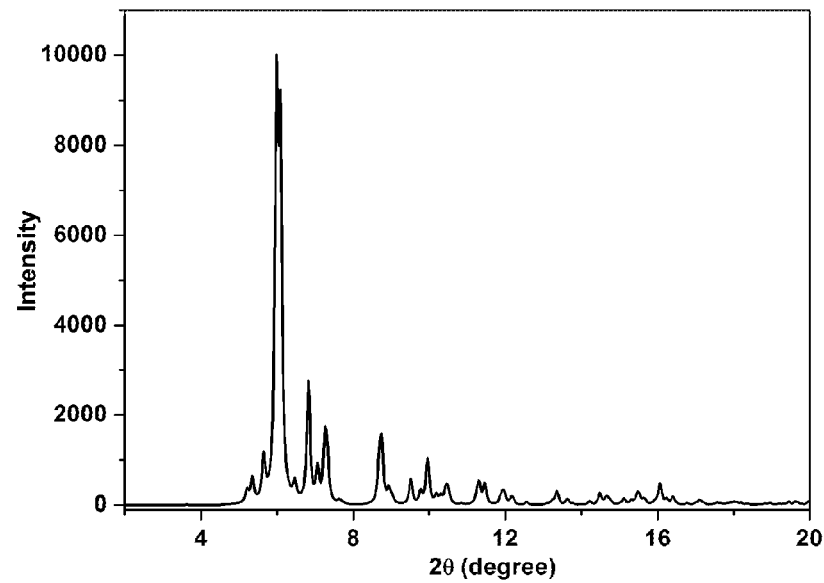
FIG. 13 shows PXRD patterns of 260-Cr(III).

The powder x-ray diffraction pattern (PXRD) for PCN-260-Cr(III) is shown in FIG. 13.

PCN-333-Cr(III)—Example 3 (PSRMO)

Synthesis of PCN-333-Cr(III)

Synthesis of PCN-333(Fe): TATB (50 mg) and anhydrous $FeCl_3$ (60 mg) were dissolved in 10 mL DEF or DMF, then 0.5 mL trifluoroacetic acid was added. The mixture was heated up in 150° C. oven for 12 h until brown precipitate formed.

The brown precipitate was centrifuged and washed with fresh DMF for several times. Yield (based on ligand): 85%.

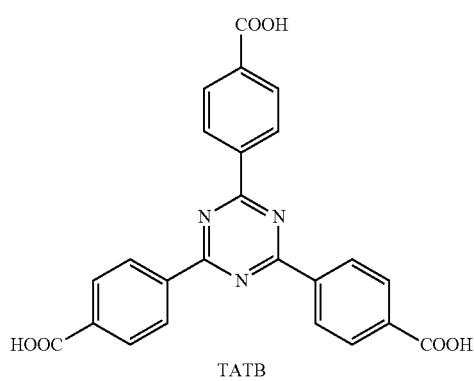

TATB

Synthesis 1 of PCN-333(Cr): 50 mg of PCN-333(Fe) and 10 mg $CrCl_2$ are mixed in 5 mL DMF and heated up at 80° C. for 4 hours. After removing Then the solvent is removed and product is washed with fresh DMF for several times. Green product is obtained.

Yield: 99%.

PCN-333-Cr(III)—Example 4 (PSRMO)

Synthesis of PCN-3'-Cr(III)

$FeCl_3$ (60 mg), $H_3TATB$ (60 mg), DEF (10 mL) and TFA (0.5 mL) were mixed in a 20 mL vial. The solids were supersonically dissolved and the vial was heated at 150° C. for 12 hours. The resulting solid was centrifuged and washed with anhydrous DMF for several times. 10 mL of anhydrous DMF was added into the vial and the mixture was degassed with nitrogen for 2 hours. 120 mg $CrCl_2$ was added into the vial in a glove box. Then the vial was heated at 85° C. for about 30 minutes until all of the solids turned green. Then the vial was centrifuged and transferred into the glove box to discard the mother liquor followed by rinsing with anhydrous DMF for three times. The vial was taken out of the glove box and rinsed with DMF twice in the air. For sample activation, the sample was rinsed with acetone twice, dried in a 85° C. oven, activated at 150° C. for 5 hours.

Figure 14:
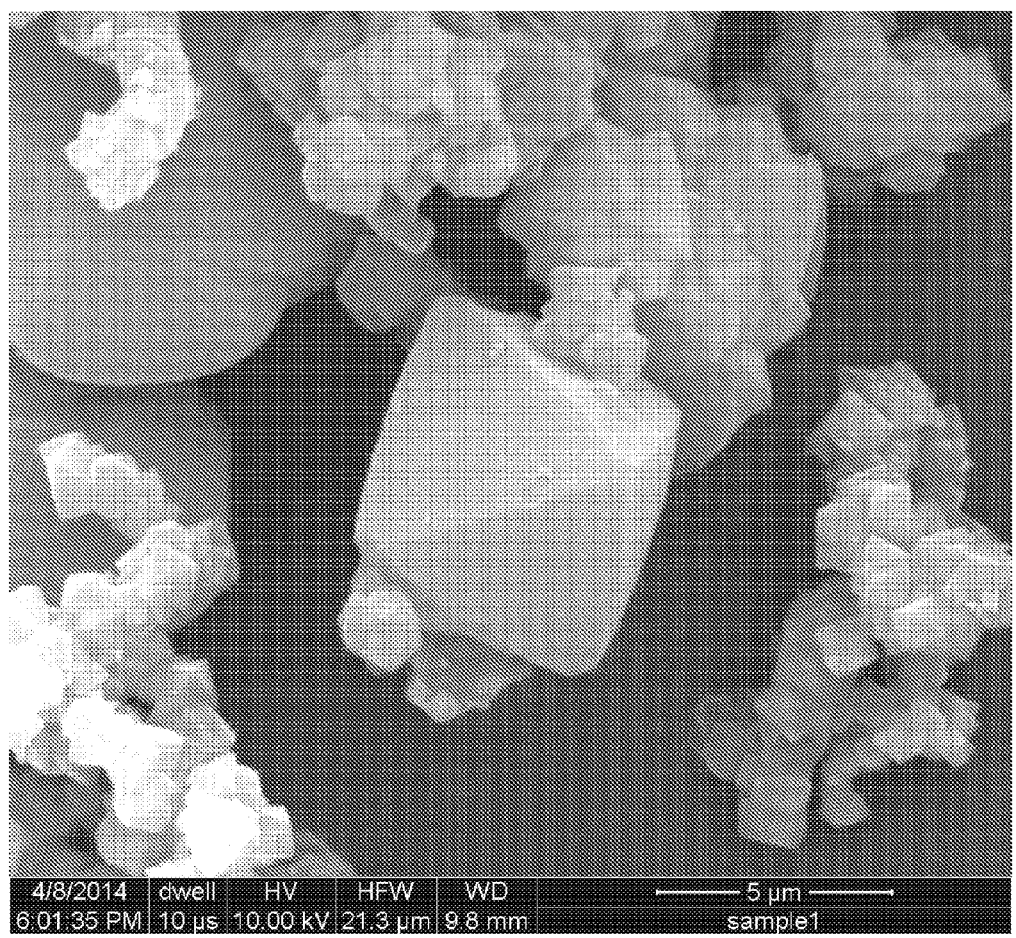
FIG. 14 shows an optical microscope image of PCN-333-Cr(III).

An optical microscope image of PCN-333-Cr(III) is shown in FIG. 14.

Stability Test 60 mg solid was suspended in 10 mL aqueous solution at different pH values for 24 hours under room temperature. The solid was collected by centrifuge and was rinsed by acetone three times, dried at 85° C., and activated at 150° C. for 5 hours.

Gas Adsorption Measurement

The adsorption characteristics of PCN-333-Cr(III) obtained via Synthesis 2 were measured.

Before measurements were carried out, as-synthesized samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2Cl_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

FIG. 15 shows the $N_2$ uptake (adsorption) measured for PCN-333-Cr(III) obtained via Synthesis 2.

Thermogravimetric Analysis

About 15 mg samples were was heated on a TGA-50 (Shimadzu) thermogravimetric analyzer from room temperature to 600° C. at a rate of 2° C. $min^{-1}$ under $N_2$ flow of 15 mL $min^{-1}$.

Figure 16:
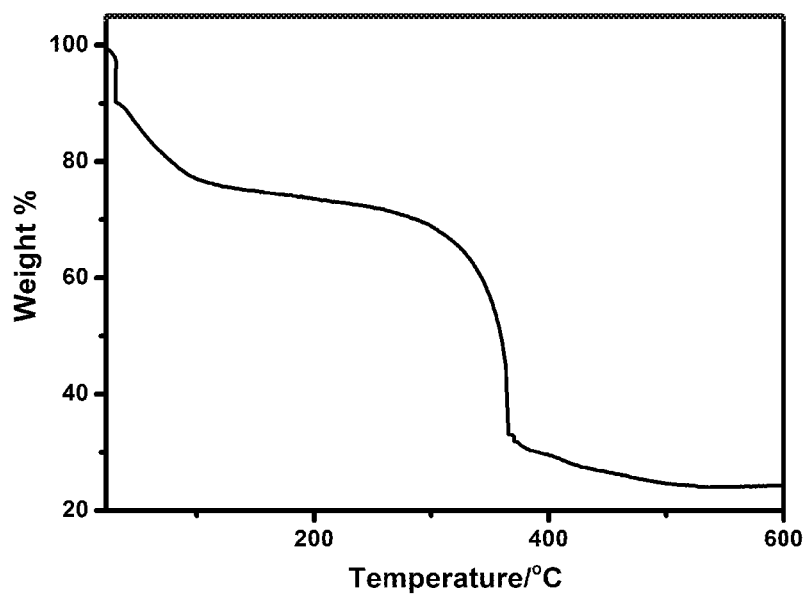
FIG. 16 shows the thermograyimetric (TG) analyses for as-synthesized PCN-333-Cr(III).

FIG. 16 shows the thermogravimetric analysis trace for a fresh sample of PCN-333-Cr(III) obtained via Synthesis 2.

Powder X-Ray Diffraction Pattern

Figure 17:
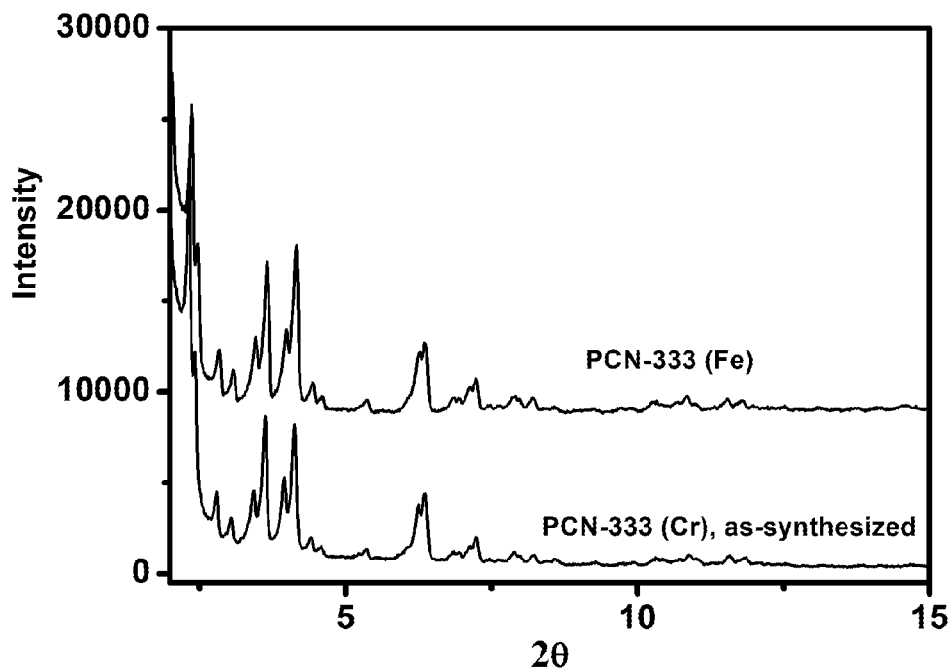
FIG. 17 shows PXRD patterns of PCN-333-Cr(III) and PCN-333-Fe.

The powder x-ray diffraction pattern (PXRD) for PCN-333-Cr(III) obtained via Synthesis 2 is shown in FIG. 17.

Preparation of PEI-incorporated PCN-333-Cr(III) and PEI-incorporated PCN-333-Fe(III)

60 mg activated PCN-333-Cr(III) was suspended in anhydrous dichloromethane (5 mL) and 300 mg PEI was slowly added in the slurry. The mixture was well mixed by gentle shaking for 20 minutes. The solid was separated by centrifuge and the excess PEI was washed by dichloromethane. The sample was first dried under vacuum and activated at 80° C. for 1 hour. PEI-incorporated PCN-333-Fe(III) was obtained in the same manner as PEI-incorporated PCN-333-Cr(III).

PCN-333-Ti(IV)
Synthesis of PCN-333-Ti(IV)

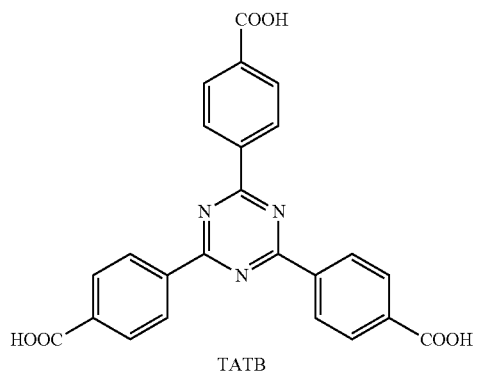

TATB

Synthesis of PCN-333-Sc: $ScCl_3 \cdot 6H_2O$ (40 mg), TATB (15 mg) and trifluoroacetic acid (0.1 mL) in 2 mL of DEF or DMF were ultrasonically dissolved in a 4 mL vial. The mixture was heated in 120° C. oven for 3 days. After cooling down to room temperature, white octahedral crystals were harvested in 80% yield.

Synthesis of PCN-333-Sc: $ScCl_3 \cdot 6H_2O$ (200 mg) and TATB (80 mg) were dissolved in 10 mL of DMF in a 20 mL vial. The mixture was heated in 150° C. oven for 2 hours until a white precipitate was formed. The white precipitate was centrifuged and washed with DMF. Yield: 90%.

Synthesis of PCN-333-Ti(III): After decanting mother liquid, the as-synthesized crystals of PCN-333-Sc were washed with dry DMF for three times and then immersed in dry DMF. The mixture was bubbled with nitrogen for 15 min, and subsequently transferred into gloves box. Then 100 mg $TiCl_3 \cdot 3THF$ was added to the solution. The crystals' color changed from white to purple in about one minute, and get darker and darker. The exchange procedure continued overnight at 85° C. Following the decanting of the upper liquid, the crystals were washed several times until the solution is colorless. This whole process should be kept in the gloves box.

Synthesis of PCN-333-Ti(IV): Methanol was used to exchange the DMF solvent in PCN-333-Ti(III) for three times in two days. The whole solvent exchange process was kept in the gloves box. After removing the solvent under vacuum for 1 h, the solid was left in air for 24 h to carry out the oxidation process to produce PCN-333-Ti(IV).

TABLE 3

ICP Data for PCN-333-Sc and PCN-333-Ti(IV)

| Elements | PCN-333-Sc (atomic %) | PCN-333-Ti (atomic %) |
|---|---|---|
| Scandium(Sc) | 100% | 3.9% |
| Titanium(Ti) | 0% | 96.1% |

Gas Adsorption Measurement

The adsorption characteristics of PCN-333-Ti(IV) were measured.

Before measurements were carried out, as-synthesized samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2Cl_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

Figure 18:
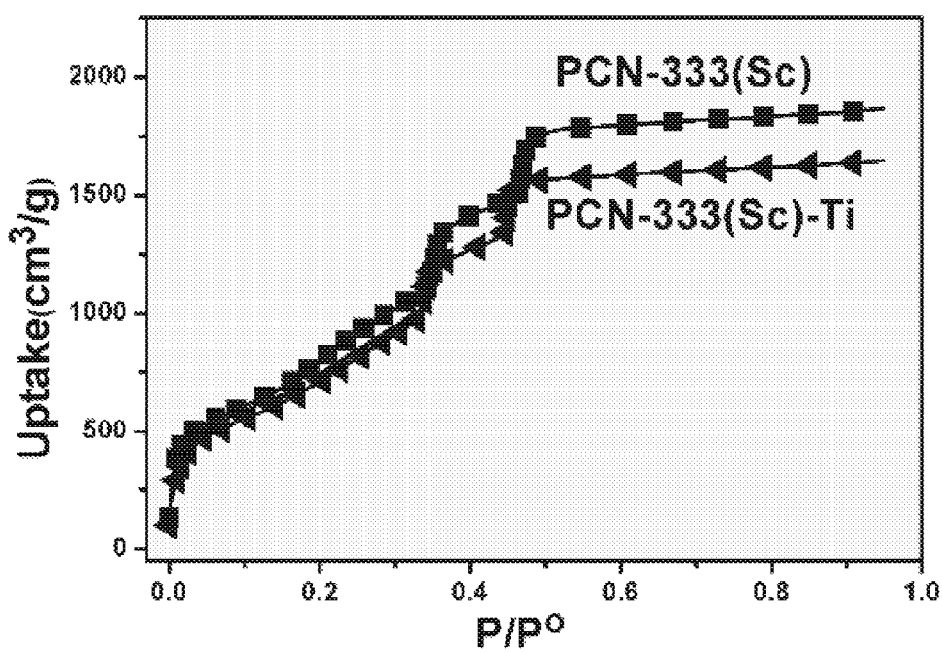
FIG. 18 shows the $N_2$ adsorption isotherm of PCN-333 (Sc)-Ti(IV) and PCN-333-Sc.

FIG. 18 shows the $N_2$ uptake (adsorption) measured for PCN-333-Ti(IV).

Thermogravimetric Analysis

About 15 mg samples were was heated on a TGA-50 (Shimadzu) thermogravimetric analyzer from room temperature to 600° C. at a rate of 2° C. $min^{-1}$ under $N_2$ flow of 15 mL $min^{-1}$.

Figure 19:
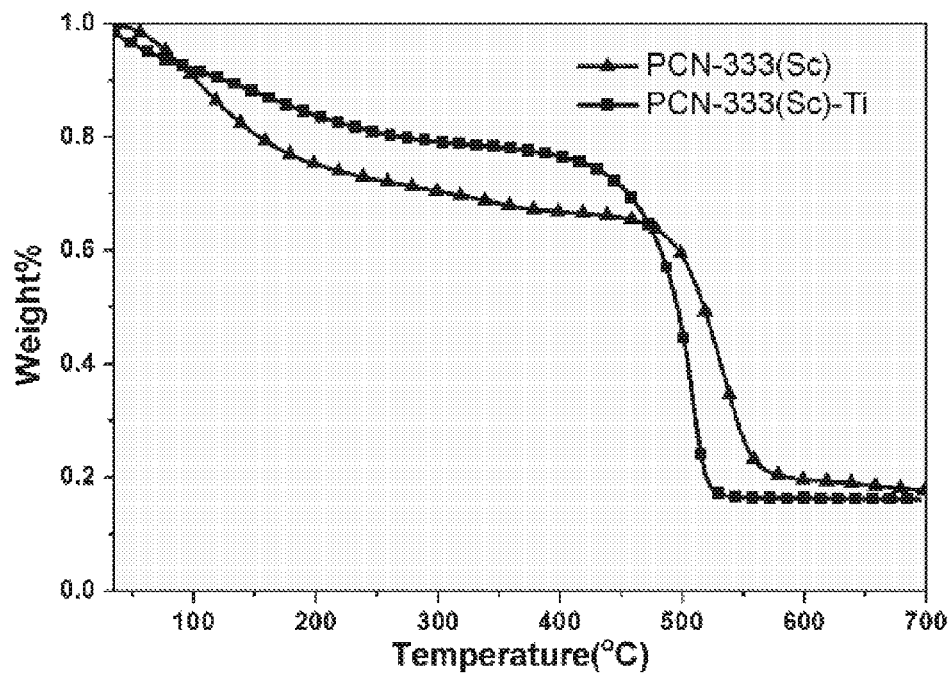
FIG. 19 shows the thermograyimetric (TG) analyses for as-synthesized PCN-333(Sc)-Ti(IV).

FIG. 19 shows the thermogravimetric analysis trace for a fresh sample of PCN-333-Ti(IV).

Powder X-Ray Diffraction Pattern

Figure 20:
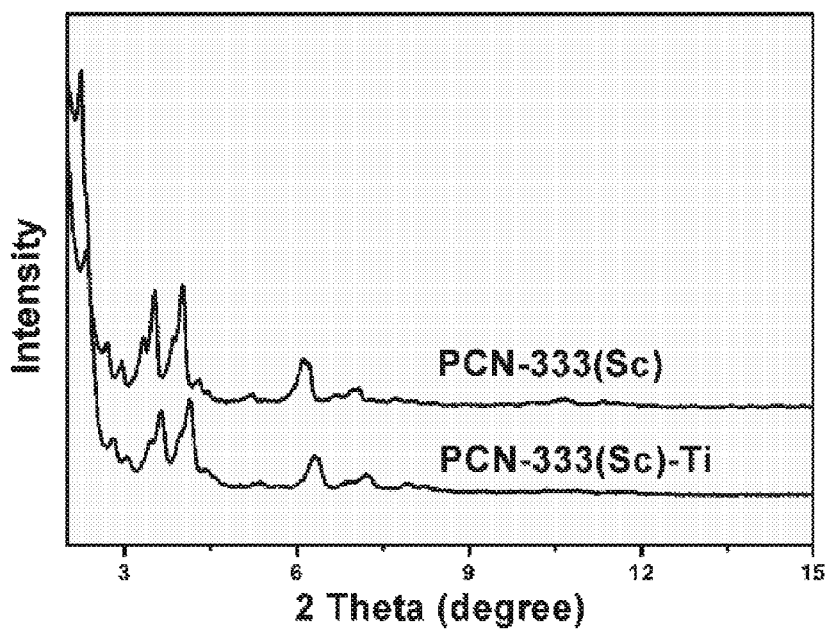
FIG. 20 shows PXRD patterns of PCN-333(Sc)-Ti(IV) and PCN-333-Sc.

The powder x-ray diffraction pattern (PXRD) for PCN-333-Ti(IV) is shown in FIG. 20.

MIL-100-Ti(IV)
Synthesis of MIL-100-Ti(IV)

Synthesis of MIL-100-Sc: $ScCl_3 \cdot 6H_2O$ (200 mg) and BTC (60 mg) were dissolved in 10 mL DMF. The mixture was heated up in 150° C. oven for 2 hours until a white precipitate was formed. The white precipitate was centrifuged and washed with fresh DMF several times. Yield: 85%.

Synthesis of MIL-100-Ti(III): As-synthesized MIL-100-Sc (30 mg) was washed with dry DMF three times. The mixture was bubbled with nitrogen for 15 min, and then transferred into a glove box where 50 mg $TiCl_3(THF)_3$ was added. The crystals' color changed to brown in 10 min. In order to facilitate the exchange rate, the reaction was allowed to continue at 120° C. for 24 hours. In the meantime, the mother liquid was exchanged with fresh $TiCl_3$ DMF solution every 8 hours. The solid was washed with oxygen/water-free DMF to get MIL-100(Ti)(III).

Synthesis of MIL-100-Ti(IV): Methanol was used to exchange the DMF solvent in MIL-100Ti(III) for 3 days before being activated at 150° C. for 5 hours. After the solvent was removed, the solid was left in air to carry out the oxidation process to produce MIL-100-Ti(IV).

MIL-100-Ti(IV) prepared using this method is also referred to throughout as MIL-100(Sc)-Ti(IV), i.e. obtained from MIL-100-Sc.

Gas Adsorption Measurement

The adsorption characteristics of MIL-100-Ti(IV) were measured.

Before measurements were carried out, as-synthesized samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2Cl_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

Figure 21:
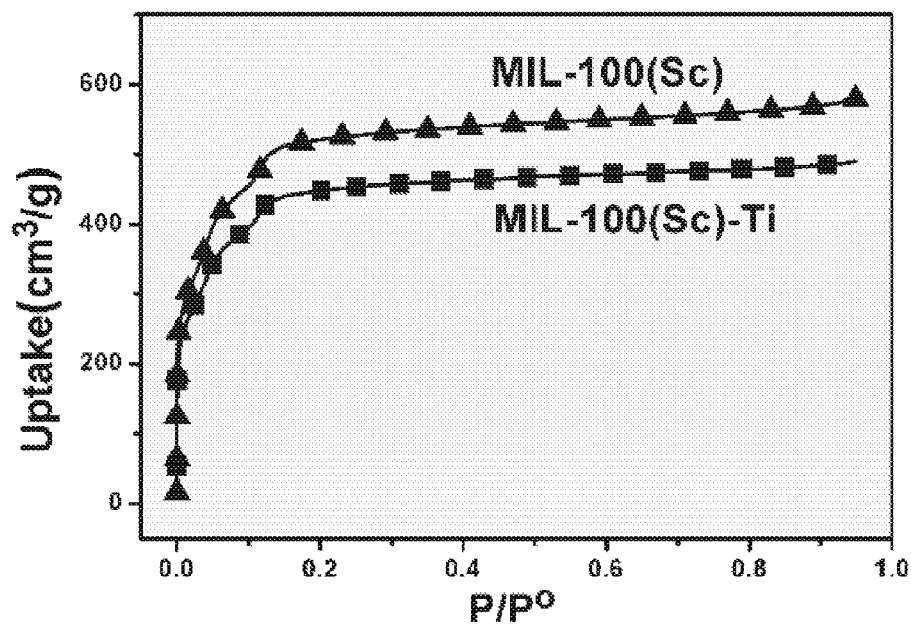
FIG. 21 shows the $N_2$ adsorption isotherm of MIL-100 (Sc)-Ti(IV) and MIL-100-Sc.

FIG. 21 shows the $N_2$ uptake (adsorption) measured for MIL-100-Ti(IV).

Thermogravimetric Analysis

About 15 mg samples were was heated on a TGA-50 (Shimadzu) thermogravimetric analyzer from room temperature to 600° C. at a rate of 2° C. min$^{-1}$ under $N_2$ flow of 15 mL min$^{-1}$.

Figure 22:
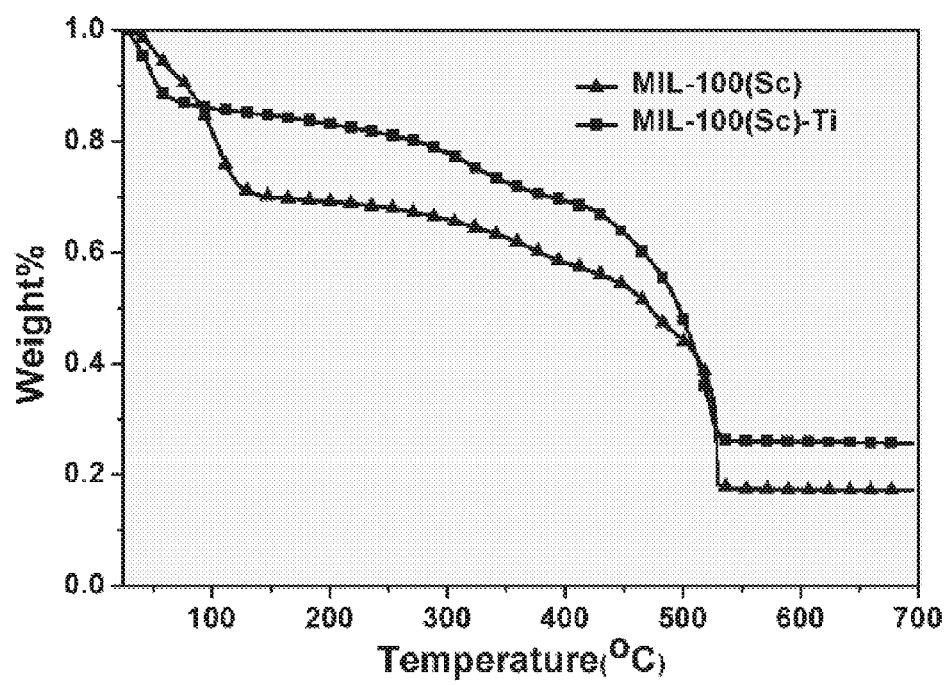
FIG. 22 shows the thermogravimetric (TG) analyses for as-synthesized MIL-100(Sc)-Ti(IV) and MIL-100-Sc.

FIG. 22 shows the thermogravimetric analysis trace for a fresh sample of MIL-100-Ti(IV).

Powder X-Ray Diffraction Pattern

Figure 23:
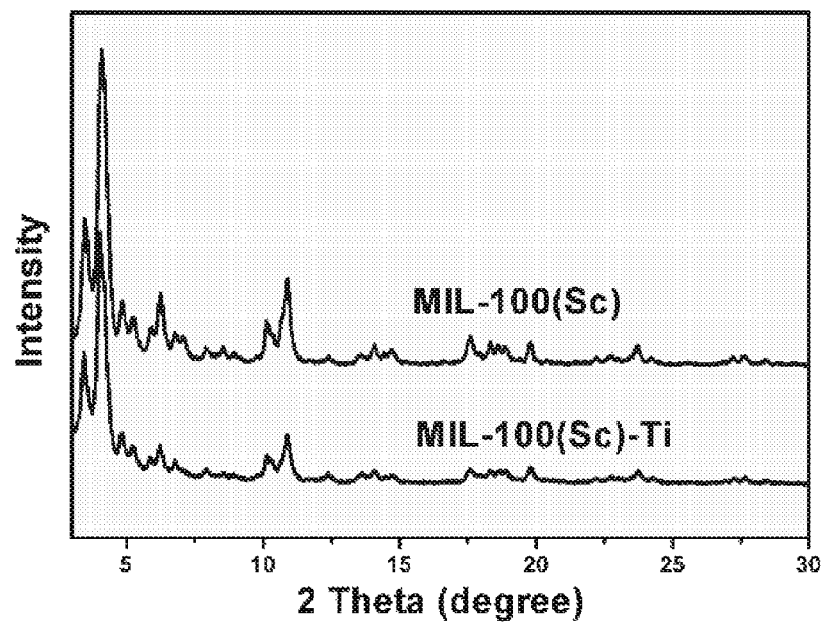
FIG. 23 shows PXRD patterns of MIL-100(Sc)-Ti(IV) and MIL-100-Sc.

The powder x-ray diffraction pattern (PXRD) for MIL-100-Ti(IV) is shown in FIG. 23.

MOF-74-Ti(IV)

Synthesis 1 of MOF-74-Ti(IV)

Synthesis of MOF-74-Zn: $Zn(NO_3)_2 \cdot 6H_2O$ (180 mg) and 2,5-dihydroxyterephthalic acid (DOBDC) (70 mg) were dissolved with 15 mL DMF in a 20 mL vial. The vial was sealed and sonicated for 10 minutes until the solid was completely dissolved. To this solution, 1 mL of ethanol followed by 1 mL of deionized water was added drop wise. The vial was sonicated resulting in a clear, yellow solution. This solution was heated in an isothermal oven at 100° C. for 24 h yielding yellow needle crystals MOF-74-Zn. Yield: 80%.

Synthesis of MOF-74-Ti(III): As-synthesized MOF-74-Zn (30 mg) was washed with dry DMF several times and immersed in dry methanol for 3 days before being activated at 130° C. for 9 hours to remove the terminal solvent molecules on the open metal sites. After activation, MOF-74-Zn was transferred into glove box where 50 mg $TiCl_3$ $(THF)_3$ in 2 mL anhydrous DMF was added. In order to ensure complete exchange, the reaction was allowed to continue at 100° C. for 18 hours. In the meantime, the mother liquid was exchanged with fresh $TiCl_3$ DMF solution every 6 hours. The crystals' color changed from light yellow to dark purple. The solid was washed with fresh oxygen/water-free DMF to get MOF-74-TI(III).

Synthesis of MOF-74-Ti(IV): Methanol was used to exchange the DMF solvent in MOF-74-TI(III) for 3 days before being activated at 60° C. for 5 hours. After this, the material was exposed to air to get oxidized to dark red MOF-74-Ti(IV).

Synthesis 2 of MOF-74-Ti(IV)

Synthesis of MOF-74-Mg: $Mg(NO_3)_2 \cdot 6H_2O$ (150 mg) and DOBDC (600 mg) were dissolved with 15 mL DMF in a 20 mL vial. The vial was sealed and sonicated for 10 minutes until the solid was completely dissolved. To this solution, 1 mL of ethanol and 1 mL of deionized water was added. The vial was sonicated resulting in a clear, light yellow solution. This solution was heated in an isothermal oven at 120° C. for 24 h yielding yellow needle crystals MOF-74-Mg. Yield: 75%.

Synthesis of MOF-74-Ti(III): As-synthesized MOF-74-Mg (30 mg) was washed with dry DMF several times and immersed in dry methanol for 3 days before being activated at 130° C. for 9 hours to remove the terminal solvent molecules on the open metal sites. The activated MOF-74-Mg was transferred into a glove box where 60 mg $TiCl_3$ $(THF)_3$ in 2 mL anhydrous DMF was added. In order to ensure complete exchange, the reaction was allowed to continue at 120° C. for 36 hours. In the meantime, the mother liquid was exchanged with fresh $TiCl_3$ DMF solution every 6 hours. The crystals' color changed from yellow to black. The solid was washed with fresh oxygen/water-free DMF to get MOF-74-Ti(III).

Synthesis of MOF-74-Ti(IV): Methanol was used to exchange the DMF solvent in MOF-74-Ti(III) for 3 days before being activated at 60° C. for 5 hours. After this, the material was exposed to air to get oxidized to orange MOF-74-Ti(IV).

Gas Adsorption Measurement

The adsorption characteristics of MOF-74-Ti(IV) were measured.

Before measurements were carried out, as-synthesized samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry $CH_2Cl_2$ several times, and $CH_2Cl_2$ solvent exchange was conducted under a well-sealed vial at 60° C. for 3 days. After that, the solvent was removed on a vacuum line and the sample was transported in a glove box to prevent the re-adsorption of $H_2O$ from the air. The sample was then activated again using the 'outgas' function of the adsorption instrument for 12 h at 190° C. Gas adsorption was then measured.

Figure 24:
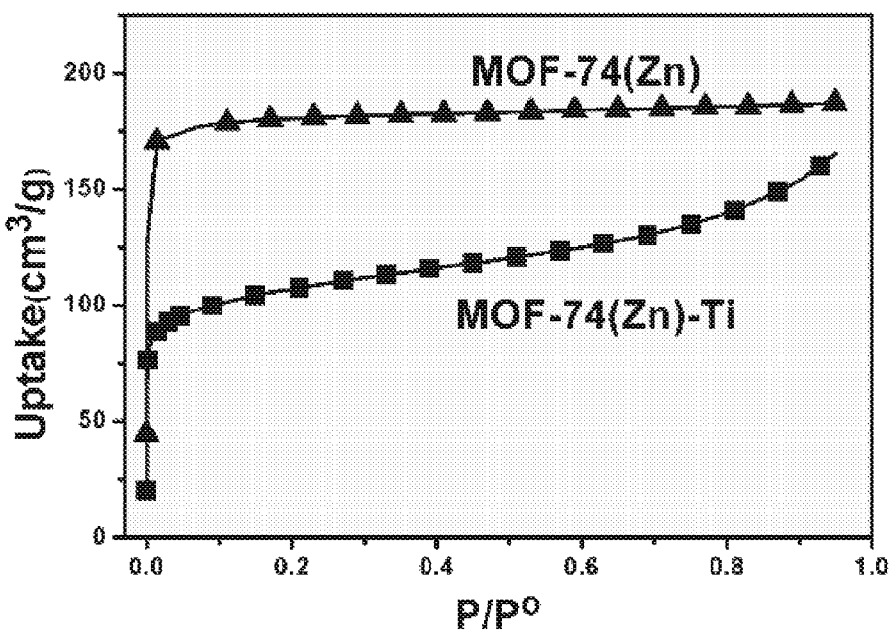
FIG. 24 shows the $N_2$ adsorption isotherm of MOF-74 (Zn)-Ti(IV).

FIG. 24 shows the $N_2$ uptake (adsorption) measured for MOF-74(Zn)-Ti(IV), i.e. MOF-74-Ti(IV) prepared using Synthesis 1 above.

Figure 25:
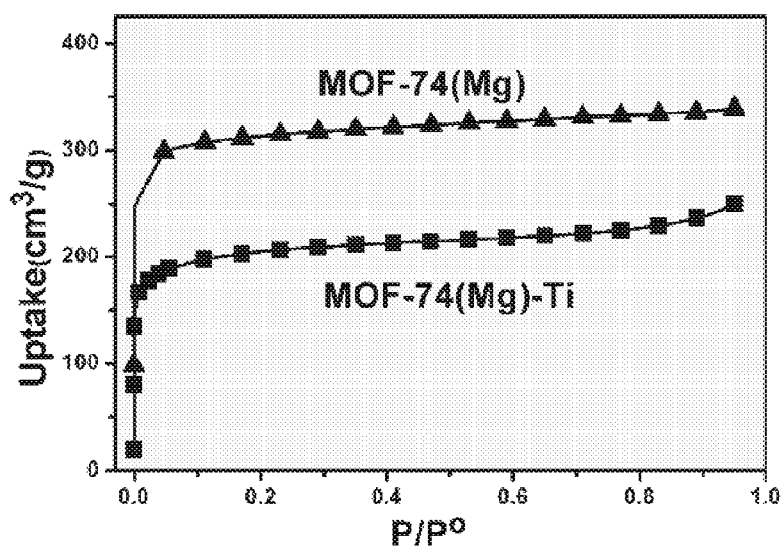
FIG. 25 shows the $N_2$ adsorption isotherm of MOF-74 (Mg)-Ti(IV) and MOF-74-Mg.

FIG. 25 shows the $N_2$ uptake (adsorption) measured for MOF-74(Mg)-Ti(IV), i.e. MOF-74-Ti(IV) prepared using Synthesis 2 above.

Thermogravimetric Analysis

About 15 mg samples were was heated on a TGA-50 (Shimadzu) thermogravimetric analyzer from room temperature to 600° C. at a rate of 2° C. min$^{-1}$ under $N_2$ flow of 15 mL min$^{-1}$.

Figure 26:
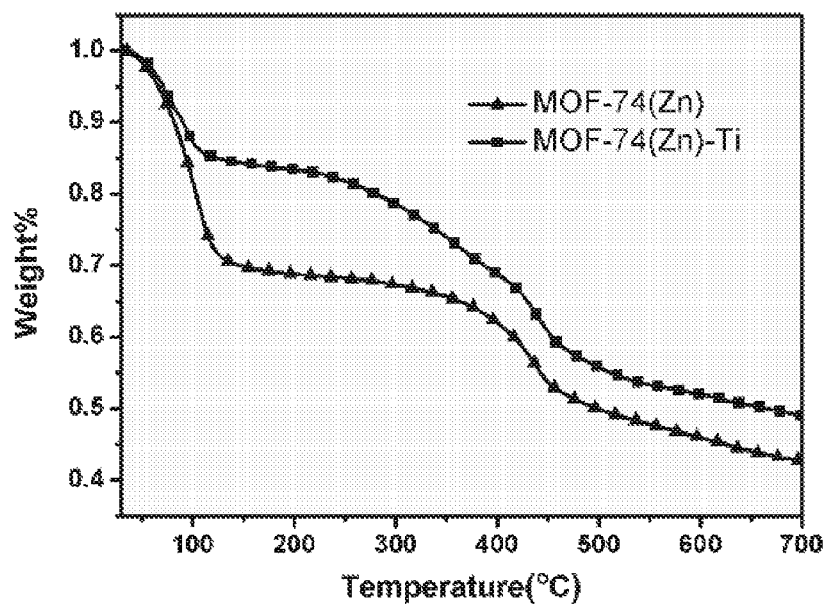
FIG. 26 shows the thermogravimetric (TG) analyses for as-synthesized MOF-74(Zn)-Ti(IV) and MOF-74-Zn.

FIG. 26 shows the thermogravimetric analysis trace for a fresh sample of MOF-74(Zn)-Ti(IV).

Figure 27:
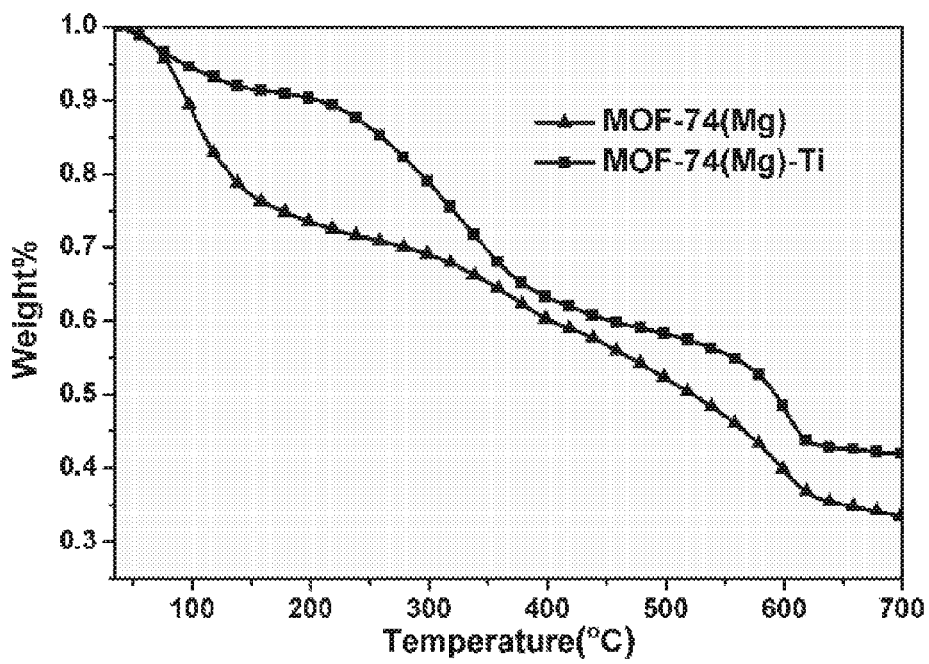
FIG. 27 shows the thermogravimetric (TG) analyses for as-synthesized MOF-74(Mg)-Ti(IV) and MOF-74-Mg.

FIG. 27 shows the thermogravimetric analysis trace for a fresh sample of MOF-74(Mg)-Ti(IV).

Powder X-Ray Diffraction Pattern

Figure 28:
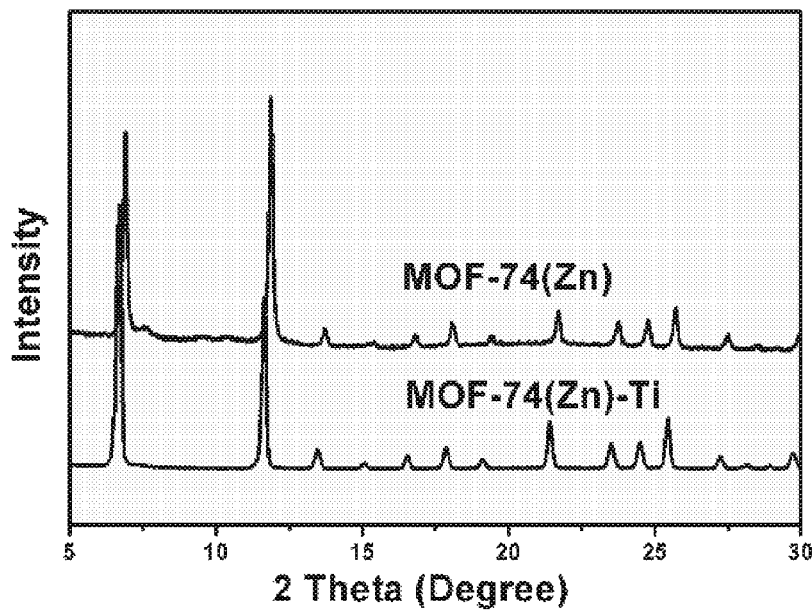
FIG. 28 shows PXRD patterns of MOF-74(Zn)-Ti(IV) and MOF-74-Zn.

The powder x-ray diffraction pattern (PXRD) for MOF-74(Zn)-Ti(IV) is shown in FIG. 28.

Figure 29:
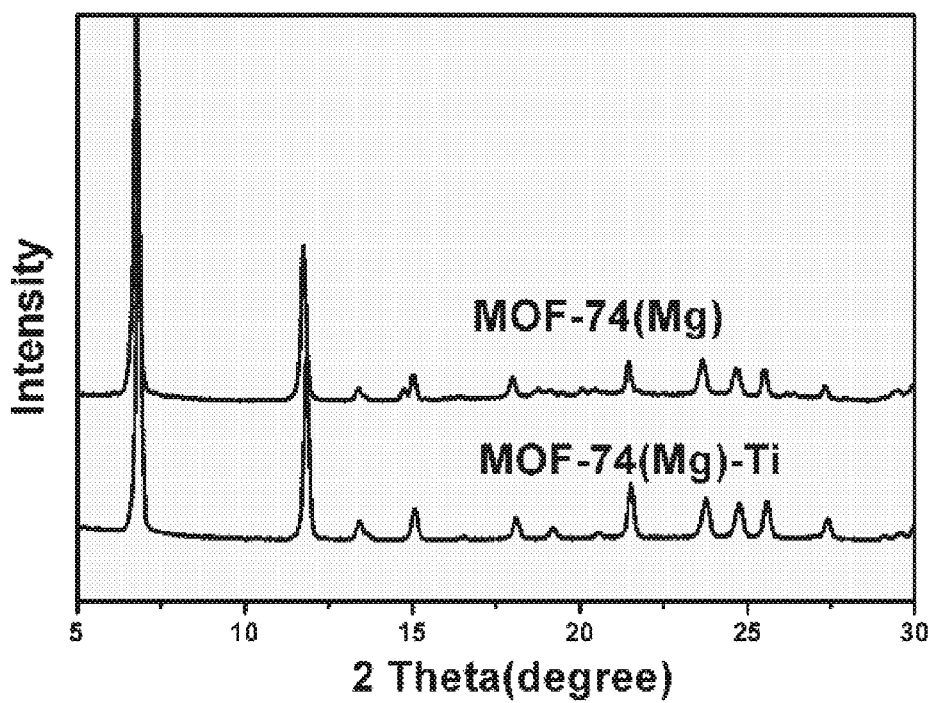
FIG. 29 shows PXRD patterns of MOF-74(Mg)-Ti(IV) and MOF-74-Mg.
Figure 30:
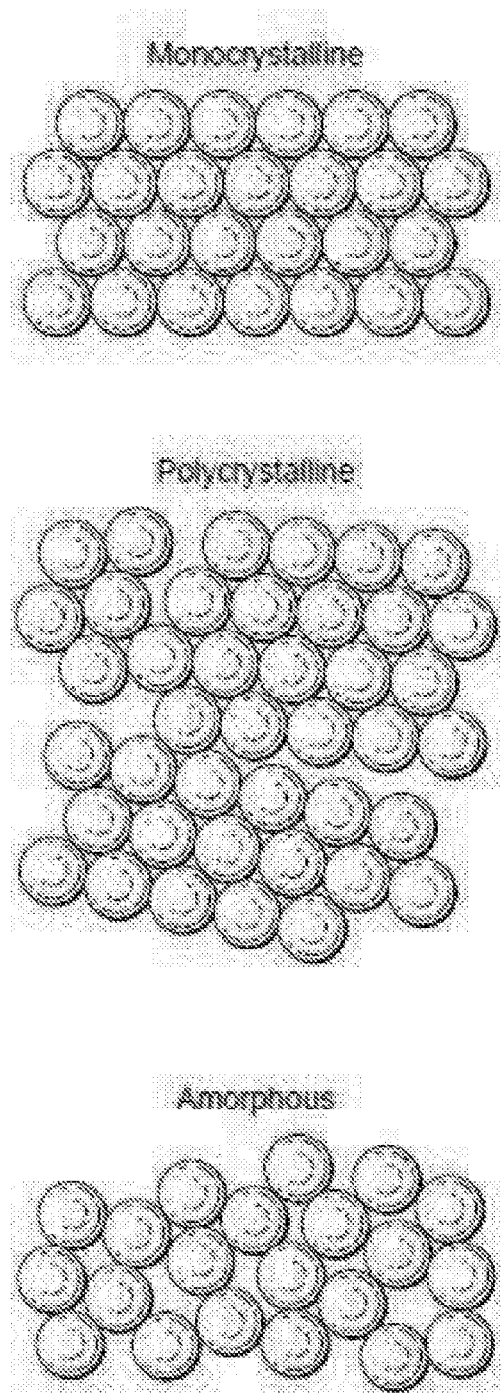
FIG. 30 illustrates the differences between amorphous, polycrystalline, and monocrystalline materials.

The powder x-ray diffraction pattern (PXRD) for MOF-74(Mg)-Ti(IV) is shown in FIG. 29.

The invention claimed is:

1. A monocrystalline metal organic framework comprising $Cr^{3+}$ ions and carboxylate ligands, wherein the monocrystalline metal organic framework has a crystal size of greater than or equal to 0.1 mm, a free diameter of about 4Å to about 60Å, and a pore volume from about 0.1 cm$^3$/g to about 4 cm$^3$/g.

2. The monocrystalline metal organic framework of claim 1, wherein the metal organic framework comprising $Cr^{3+}$ ions is octahedrally coordinated, wherein three $Cr^{3+}$ ions share a common oxygen to form a $[Cr_3(\mu\text{-O})]$ cluster, and wherein each $[Cr_3(\mu\text{-O})]$ cluster is connected with four carboxylate ligands and four aqua ligands.

3. The monocrystalline metal organic framework of claim 1, having a crystal size of greater than about 0.9 mm.

4. The monocrystalline metal organic framework of claim 1, having a surface area of greater than or equal to 1200 m$^2$/g.

5. The monocrystalline metal organic framework of claim 1, having a surface area of less than or equal to 6000 m$^2$/g.

6. The monocrystalline metal organic framework of claim 1, having a free diameter of about 5Å to about 50Å.

7. The monocrystalline metal organic framework of claim 1, having a pore volume from about 0.2 cm$^3$/g to about 2 cm$^3$/g.

8. The monocrystalline metal organic framework of claim 1, wherein the carboxylate ligands are selected from 2',3",5",6'-tetramethyl-[1,1':4',1":4",1'''-quaterphenyl]3,3''',5,5'''-tetracarboxylate ligands, 1,3,5-benzenetribenzoate ligands, and 4,4',4"-s-triazine-2,4,6-triyltribenzoate ligands.

9. The monocrystalline metal organic framework of claim 1, wherein monocrystalline metal organic framework has the chemical formula $Cr_3C_{32}H_{25}O_{12}$.

10. The monocrystalline metal organic framework of claim 1, wherein the monocrystalline metal organic framework has a crystal size of 0.1 mm to 5 mm.

* * * * *